US011555191B2

(12) United States Patent
Quivy et al.

(10) Patent No.: US 11,555,191 B2
(45) Date of Patent: Jan. 17, 2023

(54) INHIBITOR FOR USE FOR PREVENTING AND/OR TREATING AN INFECTION WITH HEPATITIS B VIRUS

(71) Applicants: INSTITUT NATIONAL DE LA SANTE ET DE LA RECHERCHE MEDICALE (INSERM), Paris (FR); HOSPICES CIVILS DE LYON, Lyons (FR); Centre Léon-Bérard, Lyons (FR); Centre national de la recherche scientifique, Paris (FR); Université Claude Bernard Lyon 1, Villeurbanne (FR)

(72) Inventors: Jean Pierre Quivy, Paris (FR); Barbara Testoni, Lyons (FR); Fabien Zoulim, Villeurbanne (FR); Maelle Locatelli, Lyons (FR)

(73) Assignees: INSTITUT NATIONAL DE LA SANTE ET DE LA RECHERCHE MEDICALE (INSERM), Paris (FR); HOSPICES CIVILS DE LYON, Lyons (FR); CENTRE LÉON-BÉRARD, Lyons (FR); CENTRE NATIONAL DE LA RECHERCHE SCIENTIFIQUE, Paris (FR); UNIVERSITÉ CLAUDE BERNARD LYON 1, Villeurbanne (FR)

( * ) Notice: Subject to any disclaimer, the term of this patent is extended or adjusted under 35 U.S.C. 154(b) by 0 days.

(21) Appl. No.: 16/643,293

(22) PCT Filed: Aug. 31, 2018

(86) PCT No.: PCT/EP2018/073535
§ 371 (c)(1),
(2) Date: Feb. 28, 2020

(87) PCT Pub. No.: WO2019/043193
PCT Pub. Date: Mar. 7, 2019

(65) Prior Publication Data
US 2020/0377892 A1    Dec. 3, 2020

(30) Foreign Application Priority Data
Sep. 1, 2017 (EP) .................................... 17306134

(51) Int. Cl.
*C12N 15/113* (2010.01)

(52) U.S. Cl.
CPC ...... *C12N 15/1131* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| 9,677,076 B2 | 6/2017 | Swayze et al. |
| 2010/0183652 A1* | 7/2010 | Page ............... C07K 14/005 424/189.1 |

OTHER PUBLICATIONS

Placek et al. Journal of Virology 83, p. 1416-1421 (Year: 2009).*
Rai et ail Nucleic Acid Research 45, 11673-11683 (Year: 2017).*
Hagedorn et al. Nucleic Acid Research vol. 45, pp. 2262-2282 (Year: 2017).*
Fakhr et al. Cancer Gene Therapy 23, 73-82 (Year: 2016).*
Billioud Gaetan et al.: "In vivo reduction of hepatitis B virus antigenemia and viremia by anti sense oligonucleotides", Journal of Hepatology, vol. 64, No. 4, Apr. 2016 (Apr. 2016), pp. 781-789, XP029448832, ISSN: 0168-8278, DOI: 10.1016/J.JHEP.2015.11.032 the whole document.
Gaetan Billioud et al.: "In vivo reduction of hepatitis B virus antigenemia and viremia by antisense oligonucleotides", Journal of Hepatology, vol. 64, No. 4, Apr. 1, 2016 (Apr. 1, 2016), pp. 781-789, XP055445356, Amsterdam, NL ISSN: 0168-8278, DOI: 10.1016/j.jhep.2015.11.032 the whole document.
Mohube Maepa et al.: "Progress and prospects of anti-HBV gene therapy development", International Journal of Molecular Sciences, vol. 16, No. 8, Jul. 31, 2015 (Jul. 31, 2015), pp. 17589-17610, XP055444220, DOI: 10.3390/ijms160817589 the whole document.
Kazuto Tajiri et al.: "New horizon for radical cure of chronic hepatitis B virus infection", World Journal of Hepatology, vol. 8, No. 21, Jan. 1, 2016 (Jan. 1, 2016), p. 863, XP055444225, ISSN: 1948-5182, DOI: 10.4254/wjh.v8.i21.863 the whole document.
International Search Report for PCT/EP2018/072338, dated Oct. 9, 2018.
Written Opinion of the International Searching Authority for PCT/EP2018/072338, dated Oct. 9, 2018.
European Search Report for EP17306134, dated Jan. 29, 2018.

* cited by examiner

*Primary Examiner* — Brian Whiteman
(74) *Attorney, Agent, or Firm* — WCF IP

(57) ABSTRACT

An inhibitor for use for preventing and/or treating an infection with hepatitis B virus (HBV) and an in vitro screening method for the identification of a candidate compound suitable for preventing and/or treating an infection with hepatitis B virus is provided.

Figure 1:
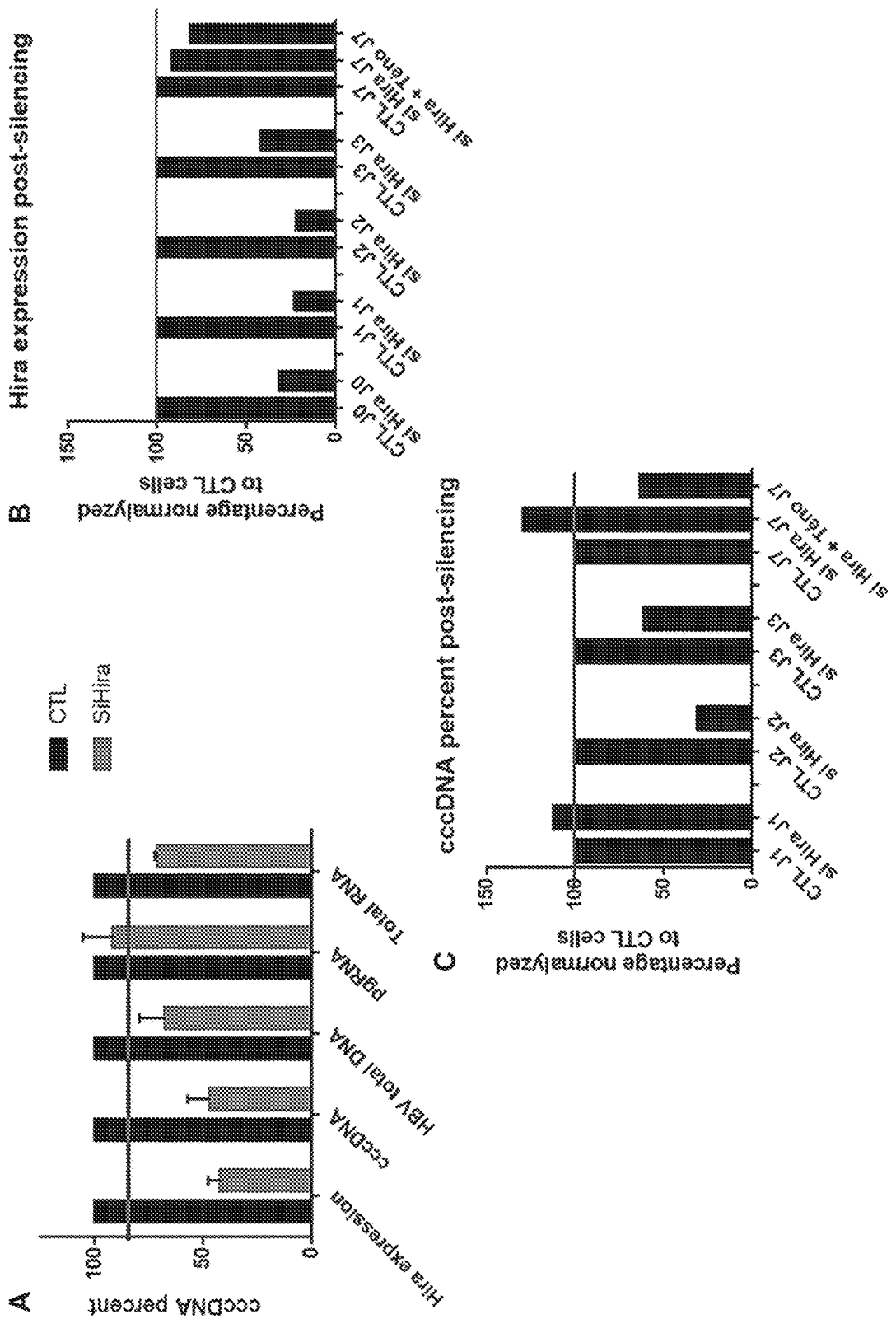

15 Claims, 13 Drawing Sheets
Specification includes a Sequence Listing.

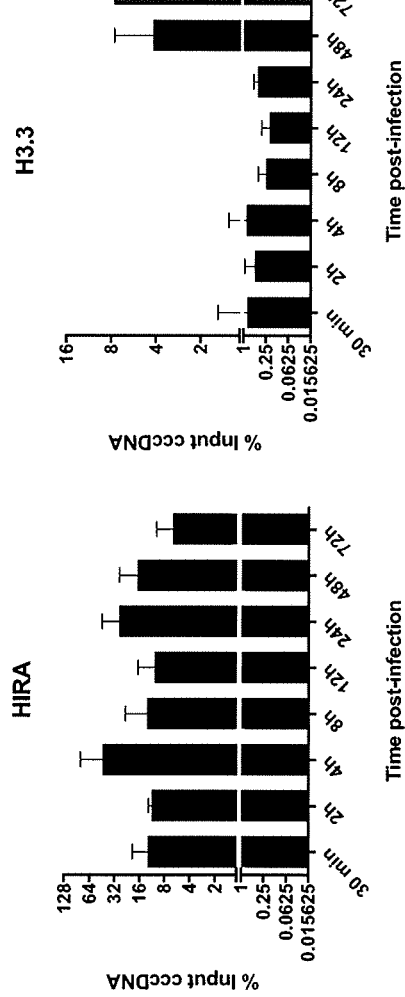
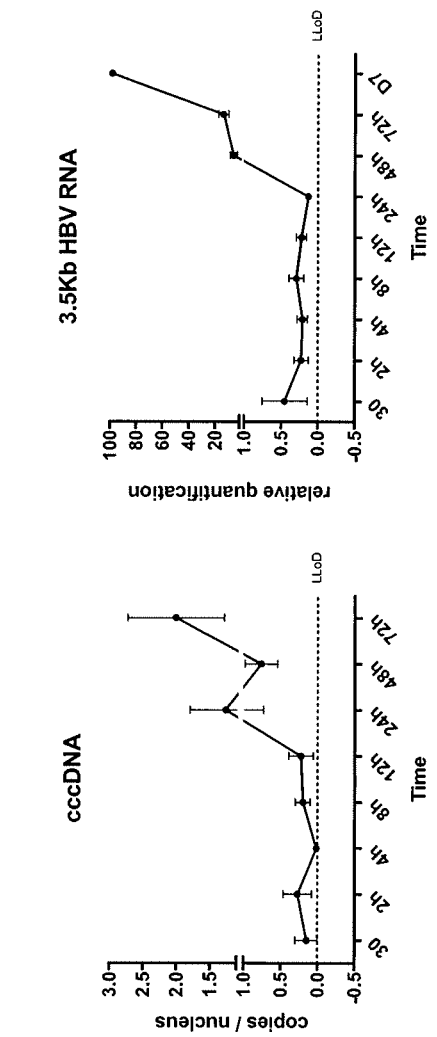

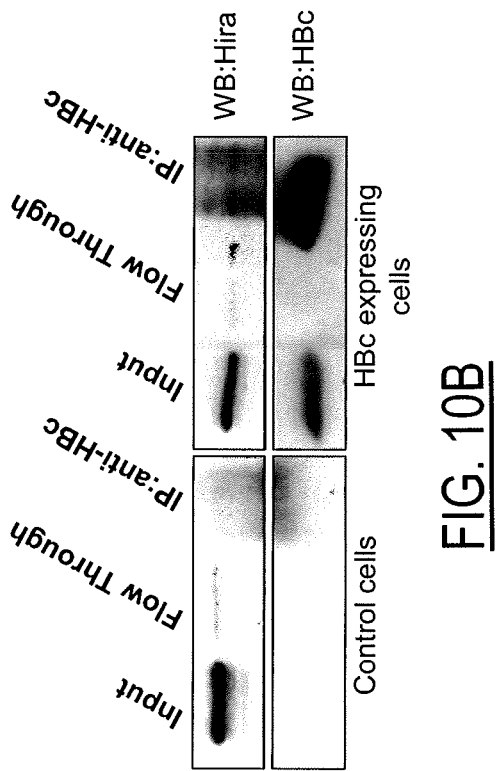
FIG. 10B
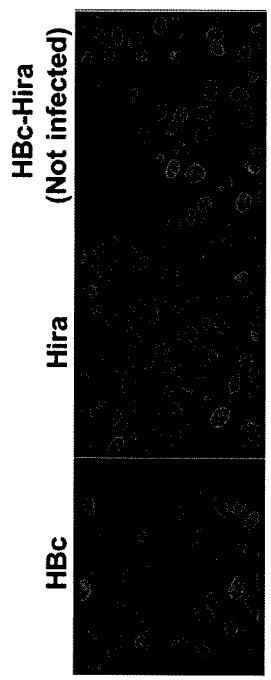
FIG. 10A
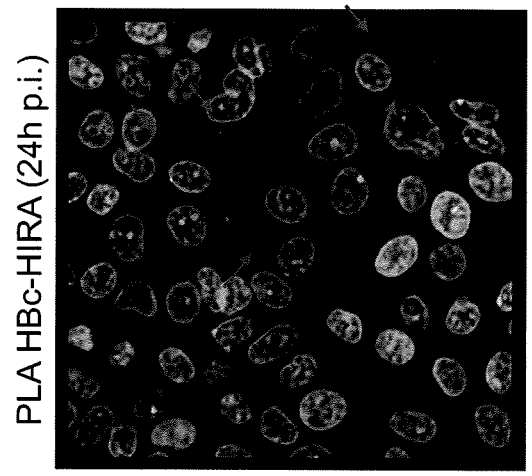
FIG. 10C
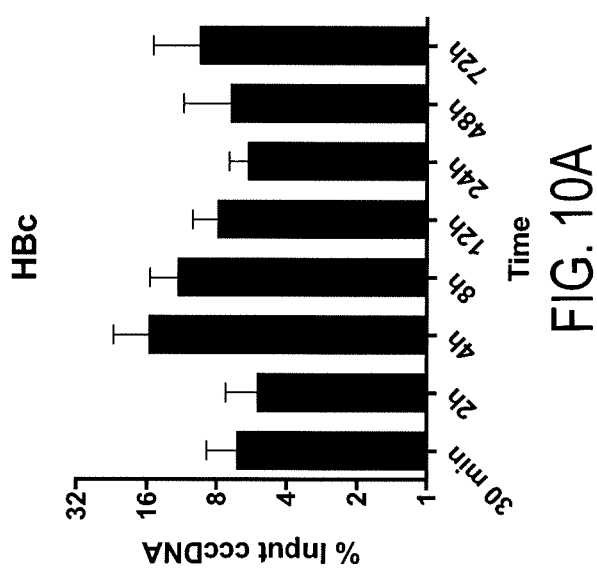

SEQUENCE LISTING

```
<160> NUMBER OF SEQ ID NOS: 36

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
ggauaacacu gucgucauc                                                  19

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
ggcctcggaa ggactctc                                                   18

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agacagacac atggcctcct                                                 20

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ccgtgtgcac ttcgcttca                                                  19

<210> SEQ ID NO 5
<211> LENGTH: 19
<212> TYPE: DNA
<213> ORGANISM: Artificial Sequence
<220> FEATURE:
<223> OTHER INFORMATION: Primer
```

```
<400> SEQUENCE: 5
gcacagcttg gaggcttga                                              19

<210> SEQ ID NO 6
<211> LENGTH: 23
<212> TYPE: DNA
<213> ORGANISM: Artificial Sequence
<220> FEATURE:
<223> OTHER INFORMATION: Probe

<400> SEQUENCE: 6
catggagacc accgtgaacg ccc                                         23

<210> SEQ ID NO 7
<211> LENGTH: 19
<212> TYPE: RNA
<213> ORGANISM: Artificial Sequence
<220> FEATURE:
<223> OTHER INFORMATION: siRNA

<400> SEQUENCE: 7
gauuaugucc gguuaugua                                              19

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ggagtgtgga ttcgcactcc t                                           21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
agattgagat cttctgcgac                                             20

<210> SEQ ID NO 10
<211> LENGTH: 27
<212> TYPE: DNA
<213> ORGANISM: Artificial Sequence
<220> FEATURE:
<223> OTHER INFORMATION: probe

<400> SEQUENCE: 10
aggcaggtcc cctagaagaa gaactcc                                     27

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
cgtggttgga gagctcattt ggaa                                        24

<210> SEQ ID NO 12
<211> LENGTH: 22
```

<212> TYPE: DNA
<213> ORGANISM: Artificial Sequence
<220> FEATURE:
<223> OTHER INFORMATION: primer

<400> SEQUENCE: 12
attccccagc actctcgtcg gt                                    22

<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
ggauaacaga cucgucauc                                        19

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tagcgcctca ttttgtgggt                                       20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cttcctgtct ggcgattggt                                       20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
taggacccct tctcgtgtta                                       20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ccgtccgaag gtttggtaca                                       20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18

| | |
|---|---|
| atgtggtatt gggggccaag | 20 |

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19

| | |
|---|---|
| ggttgcgtca gcaaacactt | 20 |

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20

| | |
|---|---|
| tggaccttt cggctcctc | 19 |

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21

| | |
|---|---|
| gggagtccgc gtaaagagag | 20 |

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22

| | |
|---|---|
| gtctgtgcct tctcatctg | 19 |

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23

| | |
|---|---|
| aggagactct aaggcttcc | 19 |

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24

| | |
|---|---|
| tactgcactc aggcaagcaa | 20 |

<210> SEQ ID NO 25
<211> LENGTH: 20
<212> TYPE: DNA
<213> ORGANISM: Artificial Sequence

```
<220> FEATURE:
<223> OTHER INFORMATION: primer

<400> SEQUENCE: 25
tgcgaatcca cactccgaaa                                              20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
agacgaaggt ctcaatcgcc                                              20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
acccacaaaa tgaggcgcta                                              20

<210> SEQ ID NO 28
<211> LENGTH: 27
<212> TYPE: DNA
<213> ORGANISM: Artificial Sequence
<220> FEATURE:
<223> OTHER INFORMATION: primer

<400> SEQUENCE: 28
ccctacttct aacctccctg ttcttat                                      27

<210> SEQ ID NO 29
<211> LENGTH: 26
<212> TYPE: DNA
<213> ORGANISM: Artificial Sequence
<220> FEATURE:
<223> OTHER INFORMATION: primer

<400> SEQUENCE: 29
cataggaggt gtatgagttg gtcgta                                       26

<210> SEQ ID NO 30
<211> LENGTH: 27
<212> TYPE: DNA
<213> ORGANISM: Artificial Sequence
<220> FEATURE:
<223> OTHER INFORMATION: primer

<400> SEQUENCE: 30
attttatttc tccaacatac tcggatt                                      27

<210> SEQ ID NO 31
<211> LENGTH: 19
<212> TYPE: DNA
<213> ORGANISM: Artificial Sequence
<220> FEATURE:
<223> OTHER INFORMATION: primer

<400> SEQUENCE: 31
gggcaggttt tggctcgta                                               19
```

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
catttacacc aaccacccaa ctatc                                              25

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
cgaaagccta taatcactgt gcc                                                23

<210> SEQ ID NO 34
<211> LENGTH: 1017
<212> TYPE: PRT
<213> ORGANISM: Homo sapiens

<400> SEQUENCE: 34

Met Lys Leu Leu Lys Pro Thr Trp Val Asn His Asn Gly Lys Pro Ile
1               5                   10                  15

Phe Ser Val Asp Ile His Pro Asp Gly Thr Lys Phe Ala Thr Gly Gly
            20                  25                  30

Gln Gly Gln Asp Ser Gly Lys Val Val Ile Trp Asn Met Ser Pro Val
        35                  40                  45

Leu Gln Glu Asp Asp Glu Lys Asp Glu Asn Ile Pro Lys Met Leu Cys
    50                  55                  60

Gln Met Asp Asn His Leu Ala Cys Val Asn Cys Val Arg Trp Ser Asn
65                  70                  75                  80

Ser Gly Met Tyr Leu Ala Ser Gly Gly Asp Asp Lys Leu Ile Met Val
                85                  90                  95

Trp Lys Arg Ala Thr Tyr Ile Gly Pro Ser Thr Val Phe Gly Ser Ser
            100                 105                 110

Gly Lys Leu Ala Asn Val Glu Gln Trp Arg Cys Val Ser Ile Leu Arg
        115                 120                 125

Asn His Ser Gly Asp Val Met Asp Val Ala Trp Ser Pro His Asp Ala
    130                 135                 140

Trp Leu Ala Ser Cys Ser Val Asp Asn Thr Val Val Ile Trp Asn Ala
145                 150                 155                 160

Val Lys Phe Pro Glu Ile Leu Ala Thr Leu Arg Gly His Ser Gly Leu
                165                 170                 175

Val Lys Gly Leu Thr Trp Asp Pro Val Gly Lys Tyr Ile Ala Ser Gln
            180                 185                 190

Ala Asp Asp Arg Ser Leu Lys Val Trp Arg Thr Leu Asp Trp Gln Leu
        195                 200                 205

Glu Thr Ser Ile Thr Lys Pro Phe Asp Glu Cys Gly Gly Thr Thr His
    210                 215                 220

Val Leu Arg Leu Ser Trp Ser Pro Asp Gly His Tyr Leu Val Ser Ala
225                 230                 235                 240

His Ala Met Asn Asn Ser Gly Pro Thr Ala Gln Ile Ile Glu Arg Glu
                245                 250                 255

```
Gly Trp Lys Thr Asn Met Asp Phe Val Gly His Arg Lys Ala Val Thr
            260                 265                 270

Val Val Lys Phe Asn Pro Lys Ile Phe Lys Lys Gln Lys Asn Gly
                275                 280                 285

Ser Ser Ala Lys Pro Ser Cys Pro Tyr Cys Cys Ala Val Gly Ser
    290                 295                 300

Lys Asp Arg Ser Leu Ser Val Trp Leu Thr Cys Leu Lys Arg Pro Leu
305                 310                 315                 320

Val Val Ile His Glu Leu Phe Asp Lys Ser Ile Met Asp Ile Ser Trp
                325                 330                 335

Thr Leu Asn Gly Leu Gly Ile Leu Val Cys Ser Met Asp Gly Ser Val
            340                 345                 350

Ala Phe Leu Asp Phe Ser Gln Asp Glu Leu Gly Asp Pro Leu Ser Glu
        355                 360                 365

Glu Glu Lys Ser Arg Ile His Gln Ser Thr Tyr Gly Lys Ser Leu Ala
    370                 375                 380

Ile Met Thr Glu Ala Gln Leu Ser Thr Ala Val Ile Glu Asn Pro Glu
385                 390                 395                 400

Met Leu Lys Tyr Gln Arg Arg Gln Gln Gln Gln Leu Asp Gln Lys
                405                 410                 415

Ser Ala Ala Thr Arg Glu Met Gly Ser Ala Thr Ser Val Ala Gly Val
                420                 425                 430

Val Asn Gly Glu Ser Leu Glu Asp Ile Arg Lys Asn Leu Leu Lys Lys
            435                 440                 445

Gln Val Glu Thr Arg Thr Ala Asp Gly Arg Arg Ile Thr Pro Leu
        450                 455                 460

Cys Ile Ala Gln Leu Asp Thr Gly Asp Phe Ser Thr Ala Phe Phe Asn
465                 470                 475                 480

Ser Ile Pro Leu Ser Gly Ser Leu Ala Gly Thr Met Leu Ser Ser His
                485                 490                 495

Ser Ser Pro Gln Leu Leu Pro Leu Asp Ser Ser Thr Pro Asn Ser Phe
            500                 505                 510

Gly Ala Ser Lys Pro Cys Thr Glu Pro Val Val Ala Ala Ser Ala Arg
            515                 520                 525

Pro Ala Gly Asp Ser Val Asn Lys Asp Ser Met Asn Ala Thr Ser Thr
530                 535                 540

Pro Ala Ala Leu Ser Pro Ser Val Leu Thr Thr Pro Ser Lys Ile Glu
545                 550                 555                 560

Pro Met Lys Ala Phe Asp Ser Arg Phe Thr Glu Arg Ser Lys Ala Thr
                565                 570                 575

Pro Gly Ala Pro Ala Leu Thr Ser Met Thr Pro Thr Ala Val Glu Arg
            580                 585                 590

Leu Lys Glu Gln Asn Leu Val Lys Glu Leu Arg Pro Arg Asp Leu Leu
        595                 600                 605

Glu Ser Ser Asp Ser Asp Glu Lys Val Pro Leu Ala Lys Ala Ser
    610                 615                 620

Ser Leu Ser Lys Arg Lys Leu Glu Leu Glu Val Glu Thr Val Glu Lys
625                 630                 635                 640

Lys Lys Lys Gly Arg Pro Arg Lys Asp Ser Arg Leu Met Pro Val Ser
                645                 650                 655

Leu Ser Val Gln Ser Pro Ala Ala Leu Thr Ala Glu Lys Glu Ala Met
            660                 665                 670
```

-continued

```
Cys Leu Ser Ala Pro Ala Leu Ala Leu Lys Leu Pro Ile Pro Ser Pro
            675                 680                 685

Gln Arg Ala Phe Thr Leu Gln Val Ser Ser Asp Pro Ser Met Tyr Ile
    690                 695                 700

Glu Val Glu Asn Glu Val Thr Val Val Gly Val Lys Leu Ser Arg
705                 710                 715                 720

Leu Lys Cys Asn Arg Glu Gly Lys Glu Trp Glu Thr Val Leu Thr Ser
                725                 730                 735

Arg Ile Leu Thr Ala Ala Gly Ser Cys Asp Val Val Cys Val Ala Cys
            740                 745                 750

Glu Lys Arg Met Leu Ser Val Phe Ser Thr Cys Gly Arg Arg Leu Leu
        755                 760                 765

Ser Pro Ile Leu Leu Pro Ser Pro Ile Ser Thr Leu His Cys Thr Gly
    770                 775                 780

Ser Tyr Val Met Ala Leu Thr Ala Ala Thr Leu Ser Val Trp Asp
785                 790                 795                 800

Val His Arg Gln Val Val Val Lys Glu Glu Ser Leu His Ser Ile
                805                 810                 815

Leu Ala Gly Ser Asp Met Thr Val Ser Gln Ile Leu Leu Thr Gln His
            820                 825                 830

Gly Ile Pro Val Met Asn Leu Ser Asp Gly Lys Ala Tyr Cys Phe Asn
        835                 840                 845

Pro Ser Leu Ser Thr Trp Asn Leu Val Ser Asp Lys Gln Asp Ser Leu
    850                 855                 860

Ala Gln Cys Ala Asp Phe Arg Ser Ser Leu Pro Ser Gln Asp Ala Met
865                 870                 875                 880

Leu Cys Ser Gly Pro Leu Ala Ile Ile Gln Gly Arg Thr Ser Asn Ser
                885                 890                 895

Gly Arg Gln Ala Ala Arg Leu Phe Ser Val Pro His Val Val Gln Gln
            900                 905                 910

Glu Thr Thr Leu Ala Tyr Leu Glu Asn Gln Val Ala Ala Ala Leu Thr
        915                 920                 925

Leu Gln Ser Ser His Glu Tyr Arg His Trp Leu Leu Val Tyr Ala Arg
    930                 935                 940

Tyr Leu Val Asn Glu Gly Phe Glu Tyr Arg Leu Arg Glu Ile Cys Lys
945                 950                 955                 960

Asp Leu Leu Gly Pro Val His Tyr Ser Thr Gly Ser Gln Trp Glu Ser
                965                 970                 975

Thr Val Val Gly Leu Arg Lys Arg Glu Leu Leu Lys Glu Leu Leu Pro
            980                 985                 990

Val Ile Gly Gln Asn Leu Arg Phe Gln Arg Leu Phe Thr Glu Cys Gln
        995                 1000                1005

Glu Gln Leu Asp Ile Leu Arg Asp Lys
    1010                1015

<210> SEQ ID NO 35
<211> LENGTH: 212
<212> TYPE: PRT
<213> ORGANISM: Hepatitis B virus

<400> SEQUENCE: 35

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30
```

```
Asp Pro Tyr Lys Glu Phe Gly Ala Ser Val Glu Leu Leu Ser Phe Leu
        35                  40                  45

Pro Ser Asp Phe Phe Pro Ser Ile Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Asn
                85                  90                  95

Leu Ala Thr Trp Val Gly Ser Asn Leu Glu Asp Pro Ala Ser Arg Glu
            100                 105                 110

Leu Val Val Ser Tyr Val Asn Val Asn Met Gly Leu Lys Ile Arg Gln
            115                 120                 125

Leu Leu Trp Phe His Ile Ser Cys Leu Thr Phe Gly Arg Glu Thr Val
        130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
    210

<210> SEQ ID NO 36
<211> LENGTH: 6
<212> TYPE: PRT
<213> ORGANISM: Hepatitis B virus

<400> SEQUENCE: 36

Cys Leu Thr Phe Gly Arg
1               5
```

INHIBITOR FOR USE FOR PREVENTING AND/OR TREATING AN INFECTION WITH HEPATITIS B VIRUS

The present invention concerns the prevention and/or treatment of an infection with hepatitis B virus and an in vitro screening method for the identification of a candidate compound suitable for preventing and/or treating an infection with hepatitis B virus.

Hepatitis B is a viral infection caused by the hepatitis B virus (HBV) that attacks the liver and can cause both acute and chronic disease. It is a worldwide major public health problem. An estimated 257 million people are living with hepatitis B virus infection (defined as hepatitis B surface antigen positive). In 2015, hepatitis B resulted in 887 000 deaths, mostly from complications (including cirrhosis and hepatocellular carcinoma).

The life cycle of hepatitis B virus is complex. Hepatitis B is a non-retroviral virus which uses reverse transcription as a part of its replication process. The virus enters the cell by binding to a receptor on the surface of the cell. The virus membrane then fuses with the host cell's membrane releasing the DNA and core proteins into the cytoplasm. Because the virus multiplies via RNA made by a host enzyme, the viral genomic DNA has to be transferred to the cell nucleus. The core proteins dissociate from the partially double stranded viral DNA (relaxed circular (rc)DNA) which is then made fully double stranded (by host DNA polymerases) and transformed into covalently closed circular DNA (cccDNA) that serves as a template for transcription of four viral mRNAs The largest mRNA, (which is longer than the viral genome), is used to make the new copies of the genome, to make the capsid core protein and the viral RNA-dependent-DNA-polymerase. These four viral transcripts undergo additional processing and go on to form progeny virions which are released from the cell or returned to the nucleus and re-cycled to produce even more copies of cccDNA. The long mRNA is then transported back to the cytoplasm where the viral P protein synthesizes DNA via its reverse transcriptase activity.

The mechanisms leading to cccDNA formation and chromatinization are still largely unknown and their elucidation would be a first step toward the identification of new therapeutic targets to impair cccDNA persistence. cccDNA chromatinization may depend on viral genome packaging by cellular histones which may be influenced by viral proteins such as HBV capsid protein (HBc) and/or HBV X protein (HBx).

Surprisingly, the inventors have discovered that chromatinization of incoming viral DNA is a very early event, requiring the histone chaperone HIRA. They showed that histone chaperone HIRA binds to cccDNA; thus the interaction between HIRA and cccDNA represents a new therapeutic target. Furthermore, while the HBV X protein (HBx) is not required for this process, HBV capsid protein (HBc) could play a major role, thus the interaction between HIRA and HBc also represents a new therapeutic target.

HIRA is a histone chaperone that preferentially places the variant histone H3.3 in nucleosomes. The gene coding for HIRA plays an important role in the formation of the senescence-associated heterochromatin foci. These foci likely mediate the irreversible cell cycle changes that occur in senescent cells. It is considered the primary candidate gene in some haploinsufficiency syndromes such as DiGeorge syndrome, and insufficient production of the gene may disrupt normal embryonic development.

According to one aspect, the invention thus concerns an histone chaperone HIRA inhibitor for use for preventing and/or treating an infection with hepatitis B virus (HBV).

The invention concerns the use of an histone chaperone HIRA inhibitor for the manufacture of a medicament for preventing and/or treating an infection with hepatitis B virus.

The invention also concerns a method for preventing and/or treating an infection with hepatitis B virus comprising administering a therapeutically effective amount of an histone chaperone HIRA inhibitor to a subject in need thereof.

The invention also concerns an in vitro screening method for the identification of a candidate compound suitable for preventing and/or treating an infection with hepatitis B virus comprising:

a) infecting hepatocytes with HBV, in the presence and in the absence of a candidate compound;

b) measuring the binding of HIRA to cccDNA or HBc in hepatocytes infected with HBV, in the presence and in the absence of the candidate compound;

c) comparing the level of binding of HIRA to cccDNA or HBc in hepatocytes infected with HBV in the presence the candidate compound, with the level of binding of HIRA to cccDNA or HBc in hepatocytes infected with HBV in the absence of the candidate compound; and d) identifying the candidate compound as suitable for preventing and/or treating an infection with hepatitis B virus if the level of binding of HIRA to cccDNA or HBc in hepatocytes infected with HBV in the presence the candidate compound is decreased compared with the level of binding of HIRA to cccDNA or HBc in hepatocytes infected with HBV in the absence the candidate.

DETAILED DESCRIPTION OF THE INVENTION

By "hepatitis B virus" or "HBV" according to the present invention, it is meant any hepatitis B virus of any serotype or genotype.

By "HIRA" is meant herein any naturally occurring isoform of the HIRA protein, allelic variants thereof, splice variants thereof and orthologous proteins. Typically, the sequence of the human HIRA protein is as set forth under Genbank Accession Number CAG30389 as of 2 Feb. 2011, or as set forth under UniProtKB accession number P54198 as of Feb. 21, 2006 and corresponds to the amino acid sequence SEQ ID NO: 34.

By "an histone chaperone HIRA inhibitor" or "HIRA inhibitor" according to the present invention, it is meant any compound that inhibits or reduces HIRA biological activity. The biological activity of HIRA depends on the expression of the HIRA coding gene and/or on the amount of the HIRA protein; on HIRA interaction with its targets, particularly HBc and cccDNA of HBV. Therefore, the HIRA inhibitor may reduce or inhibit HIRA expression, or reduce or inhibit HIRA interaction ability with its targets, particularly HBc and/or cccDNA of HBV.

"HIRA expression" also refers to events modifying HIRA mRNA transcriptionally or post-transcriptionally, by cleavage and maturation, to provide a functional HIRA, notably any reaction which results in inhibition of HIRA mRNA processing; it also includes events modifying HIRA protein during translation, as well as post-translational modifications.

An "inhibitor of HIRA expression" refers to any compound that has a biological effect to inhibit the expression of a HIRA gene and/or the expression of a HIRA protein. In one embodiment of the invention, said inhibitor of HIRA gene expression is a Small inhibitory RNA (siRNA), or an antisense oligonucleotide. Preferably said inhibitor has a nucleotide sequence having at least 80% and preferably at least 95% of complementary residues with HIRA's messenger RNA or part thereof. In one embodiment of the invention, said inhibitor of HIRA gene expression is a siRNA with a nucleotide sequence which is at least 80% 85%, 90%, and preferably at least 95% identical to the sequence GGAUAACACUGUCGUCAUC (SEQ ID NO: 1).

Nucleic acid sequence identity can be calculated by methods well-known to one of skill in the art. The percentage of identity may be calculated by performing a pairwise global alignment based on the Needleman-Wunsch alignment algorithm to find the optimum alignment (including gaps) of two sequences along their entire length, for instance using Needle, and using the DNAFULL matrix with a gap opening penalty of 10 and a gap extension penalty of 0.5.

Small inhibitory RNAs (siRNAs) can function as inhibitors of gene expression for use in the invention. Gene expression can be reduced with a small double stranded RNA (dsRNA), or a vector or construct causing the production of a small double stranded RNA, such that gene expression is specifically inhibited (i.e. RNA interference or RNAi). Methods for selecting an appropriate dsRNA or dsRNA-encoding vector are well known in the art for genes whose sequence is known.

Inhibitors of HIRA for use in the invention may be based on antisense oligonucleotide (ODNs) constructs. Antisense oligonucleotides, including antisense RNA molecules and antisense DNA molecules, would act to directly block the activity of HIRA by binding to HIRA mRNA and thus preventing binding leading to mRNA degradation. For example, antisense oligonucleotides of at least about 15 bases and complementary to unique regions of the HIRA transcript sequence can be synthesized, e.g., by conventional phosphodiester techniques and administered by e.g., intravenous injection or infusion. Methods for using antisense techniques for specifically inhibiting gene expression of genes whose sequence is known are well known in the art. It should be further noted that antisense oligonucleotides may be modified with phosphorothioate to prevent their in vivo hydrolysis by nucleases. Such modifications are well known in the art. Antisense oligonucleotides useful as inhibitors of HIRA can be prepared by known methods. These include techniques for chemical synthesis such as, e.g., by solid phase phosphoramadite chemical synthesis. They can also be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters.

As used herein, the terms "inhibitor of the interaction" means preventing or reducing the direct or indirect association of one or more molecules, nucleic acids, peptides, proteins.

As used herein, the term "inhibitor of the HIRA interaction with HBV covalently-closed-circular (ccc)DNA and/or HBV capsid protein" is a molecule which can prevent the interaction between HIRA and cccDNA and/or HBc, by competition or by fixing to one of the molecules. Preferably, the inhibitor is a chemical molecule, peptide, protein, aptamer, antibody or antibody fragment. In a particular embodiment the inhibitor is an antibody or antibody fragment.

In an embodiment the inhibitor of the HIRA interaction with HBV capsid protein is a molecule fixing to one or several amino acids of HIRA (UniProtKB accession number P54198 as available as of Feb. 21, 2006, SEQ ID NO:34) chosen among the group consisting of Leu464, Cys465 and Ile466.

In an embodiment the inhibitor of the HIRA interaction with HBV capsid protein is a molecule fixing to one or several amino acids of HBV capsid protein (UniProtKB accession number: Q89714 as of Nov. 1, 1996, SEQ ID NO:35) chosen among the group consisting of Ser78, His80, Cys136, Leu137, Thr138, Phe 139, Gly140, Arg141 and Thr171.

By "peptide", it is meant an amino acid sequence comprising from 2 to 30 amino acids. By "protein", it is meant an amino acid sequence comprising at least 31 amino acids, preferably 50 to 500 amino acids.

In a particular embodiment the peptide comprises or consist of the sequence CLTFGR (SEQ ID NO: 36).

By "antibody" it is meant immunoglobulin molecules and immunologically active portions of immunoglobulin molecules, i.e., molecules that contain an antigen binding site which immunospecifically binds an antigen. As such, the term antibody encompasses not only whole antibody molecules, but also antibody fragments as well as variants (including derivatives) of antibodies and antibody fragments. In particular, the antibody according to the invention may correspond to a polyclonal antibody, a monoclonal antibody (e.g. a chimeric, humanized or human antibody), a fragment of a polyclonal or monoclonal antibody or a diabody.

By "antibody fragments" it is meant a portion of an intact antibody, preferably the antigen binding or variable region of the intact antibody. Examples of antibody fragments include Fv, Fab, F(ab')$_2$, Fab', Fd, dAb, dsFv, scFv, sc(Fv)$_2$, CDRs, diabodies and multi-specific antibodies formed from antibodies fragments.

By "aptamers" it is meant the class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., Science, 1990, 249(4968):505-10. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., Clin. Chem., 1999, 45(9):1628-50. Then, after identifying the aptamers directed against HIRA as described above, those skilled in the art can readily select the ones inhibiting HIRA. Preferably the aptamer is an oligonucleotide or polypeptide from 10 to 30 kDa.

In a particular embodiment, the antibody, antibody fragment or aptamer according to the invention specifically binds to one or several amino acids selected among the group consisting of Leu 464, Cys465 and Ile466 of HIRA, or to one or several amino acids selected among the group consisting of Ser78, His80, Cys136, Leu137, Thr138, Phe 139, Gly140, Arg141 and Thr171 of the HBV capsid protein.

In a preferred embodiment, the antibody, antibody fragment or aptamer according to the invention specifically binds to:
- amino acids 464-466 of HIRA, or
- amino acids 78-80 of the HBV capsid protein, or
- amino acids 136-141 (SEQ ID NO: 36) of the HBV capsid protein, or
- amino acid 171 of the HBV capsid protein.

In a preferred embodiment, the antibody, antibody fragment or aptamer according to the invention specifically binds to:
- amino acids 464-466 of HIRA, or
- amino acids 136-141 (SEQ ID NO: 36) of the HBV capsid protein.

Methods for determining whether a compound is an HIRA inhibitor are well known by the person skilled in the art. For example, the person skilled in the art can assess whether a compound decreases HIRA expression. According to the invention, the "level of expression of HIRA" is determined by quantifying HIRA mRNA, or a fragment thereof, or by quantifying the amount of HIRA protein. For example the amount of HIRA mRNA can be quantified by RT-qPCR. Primers that can be used for this analysis can be primers of sequence SEQ ID NO: 2-3.

Other methods for determining whether a compound is an inhibitor of HIRA may be for example, by measuring the biological activity of HIRA, through measuring one of the phenomenon in which HIRA is known to play a role.

For instance, the inventors have demonstrated that HIRA is implicated in chromatinization of HBV in hepatocytes. Indeed, the biological activity of HIRA may be assessed through measuring cccDNA amount in hepatocytes exposed to HBV. cccDNA levels can be measured in particular by qPCR with cccDNA specific primers and a cccDNA specific probe. In particular cccDNA specific primers can be primers of sequence SEQ ID NO: 4-5 and the cccDNA specific probe can be the probe of sequence SEQ ID NO: 6. Sequences of these primers and probes (see table 1) spans on the nick in the HBV rcDNA and hybridize to its "gap region".

The inventors have demonstrated that HIRA binds to cccDNA and to HBc, other methods for determining whether a compound is an inhibitor of HIRA may be for example, by measuring the inhibition of the interaction of HIRA with cccDNA and/or HBc in presence of the compound.

TABLE 1

Primers and probes sequences

| Target | name | sequence |
| --- | --- | --- |
| HIRA | HIRA Forward | GGCCTCGGAAGGACTCTC (SEQ ID NO: 2) |
| HIRA | HIRA Reverse | AGACAGACACATGGCCTCCT (SEQ ID NO: 3) |
| cccDNA | cccDNA Taqman Forward | CCGTGTGCACTTCGCTTCA (SEQ ID NO: 4) |
| cccDNA | cccDNA Taqman Reverse | GCACAGCTTGGAGGCTTGA (SEQ ID NO: 5) |
| cccDNA | cccDNA Taqman Probe | [6FAM]CATGGAGACCACCG TGAACGCCC[BBQ] (SEQ ID NO: 6) |

In the context of the invention, the term "treating" or "treatment", refers to a therapeutic use (i.e. on a subject having a given disease) and means reversing, alleviating, inhibiting the progress of one or more symptoms of such disorder or condition. Therefore, treatment does not only refer to a treatment that leads to a complete cure of the disease, but also to treatments that slow down the progression of the disease and/or prolong the survival of the subject.

By "preventing" is meant a prophylactic use (i.e. on a subject susceptible of developing a given disease).

Preferably the HIRA inhibitor for use for preventing and/or treating an infection with hepatitis B virus is used on a subject. The "subject" or "individual" may be, for example, a human or non-human mammal, such as a rodent (mouse, rat), a feline, a canine or a primate, affected by or likely to be affected by a HBV infection. Typically, the subject is a human.

The HIRA inhibitor is advantageously formulated in a pharmaceutical composition, together with a pharmaceutically acceptable carrier.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier, excipient or diluent refers to a non-toxic solid, semi-solid or liquid filler, diluent, encapsulating material or formulation auxiliary of any type.

Pharmaceutically acceptable carriers and excipient that may be used in the compositions of this invention include, but are not limited to, ion exchangers, alumina, aluminium stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As appreciated by skilled artisans, the pharmaceutical composition is suitably formulated to be compatible with the intended route of administration. Examples of suitable routes of administration include topical route, oral route, intranasal route, intraocular route, parenteral route, and including intramuscular, subcutaneous, intravenous, intraperitoneal or local injections. The oral route can be used, provided that the composition is in a form suitable for oral administration, i.e. able to protect the active principle from the gastric and intestinal enzymes. Preferably the HIRA inhibitor for the use according to the invention is administered by topical route, oral route, intranasal route, intraocular route, parenteral route, or by intramuscular, subcutaneous, intravenous, intraperitoneal or local injections.

Preferably, the pharmaceutical composition contains carriers that are pharmaceutically acceptable for an injectable formulation. They may in particular be sterile, isotonic, saline solutions (monosodium phosphate, disodium phosphate, sodium chloride, potassium chloride, calcium chloride or magnesium chloride etc., or mixtures of such salts), or dry, in particular lyophilized, compositions which by means of the addition, as appropriate, of sterilized water or physiological saline, can form injectable solutes.

The doses used for the administration can be adapted as a function of various parameters, and in particular as a function of the mode of administration used, of the relevant pathology, or alternatively of the desired duration of treatment. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

It is routine for those skilled in the art to adjust the nature and amount of excipients in the pharmaceutical composition so as not to affect the desired properties thereof, notably with regard to the stability of the HIRA inhibitor according to the invention, and the route of administration considered.

Preferably, an effective amount, preferably a therapeutically effective amount of the HIRA inhibitor of the invention is administered. An "effective amount" refers to an amount effective, at dosages and for periods of time necessary, to achieve the desired therapeutic or prophylactic result.

A "therapeutically effective amount" of a HIRA inhibitor of the invention may vary according to factors such as the disease state, age, sex, and weight of the individual, and the ability of the HIRA inhibitor, to elicit a desired therapeutic result. A therapeutically effective amount encompasses an amount in which any toxic or detrimental effects of the HIRA inhibitor are outweighed by the therapeutically beneficial effects. A therapeutically effective amount also encompasses an amount sufficient to confer benefit, e.g., clinical benefit.

In a particular embodiment the HIRA inhibitor for the use according to the invention reduces cccDNA amount in the nucleus of hepatocytes infected with HBV. In particular the HIRA inhibitor reduces the cccDNA levels of at least 20%, preferably at least 40% and most preferably at least 50%. cccDNA levels can be measured in particular by qPCR with cccDNA specific primers and probe. In particular cccDNA specific primers can be primers of sequence SEQ ID NO: 4-5 and cccDNA specific probe can be the probe of sequence SEQ ID NO: 6.

The invention also concerns an in vitro screening method for the identification of a candidate compound suitable for preventing and/or treating an infection with hepatitis B virus comprising:

a) infecting hepatocytes with HBV, in the presence and in the absence of a candidate compound;

b) measuring the binding of HIRA to cccDNA or HBc in hepatocytes infected with HBV, in the presence and in the absence of the candidate compound;

c) comparing the level of binding of HIRA to cccDNA or HBc in hepatocytes infected with HBV in the presence the candidate compound, with the level of binding of HIRA to cccDNA or HBc in hepatocytes infected with HBV in the absence of the candidate compound; and d) identifying the candidate compound as suitable for preventing and/or treating an infection with hepatitis B virus if the level of binding of HIRA to cccDNA or HBc in hepatocytes infected with HBV in the presence the candidate compound is decreased compared with the level of binding of HIRA to cccDNA or HBc in hepatocytes infected with HBV in the absence the candidate.

Preferably the measure of the binding of HIRA to cccDNA or HBc comprises:

a) nuclear extraction of hepatocytes;

b) sonication of obtained nuclei;

c) immunoprecipitation with an antibody against HIRA or with an antibody against HBc;

d) purification of obtained immune complexes; and e) quantification of immune complexes comprising HIRA and cccDNA or HIRA and HBc.

An "immune complex" refers to the complex comprising the antibody used in step c) bound to its target. In particular the target can be bound to another molecule, in particular a binding partner of interest. In the method according to the invention immune complexes which are quantified comprise:

1) when an antibody against HIRA is used in step c), (i) an antibody against HIRA, HIRA and cccDNA, or (ii) an antibody against HIRA, HIRA and HBc, or 2) when an antibody against HBc is used in step c), an antibody against HBc, HBc, and HIRA.

In the method according to the invention, wherein the quantification of immune complexes for measuring the binding of HIRA to cccDNA is done, i.e. the quantification of immune complexes comprising an antibody against HIRA, HIRA and cccDNA is done, it is preferably by quantitative PCR using cccDNA specific primers and probe such as primers of sequence SEQ ID NO: 4-5 and probe of sequence SEQ ID NO: 6.

In the method according to the invention, wherein the quantification of immune complexes for measuring the binding of HIRA to HBc is done, i.e. the quantification of immune complexes comprising an antibody against HIRA, HIRA and HBc, or an antibody against HBc, HBc, and HIRA, is done, it is preferably by Western blot of immune complexes with an antibody against HIRA and/or by Western blot of immune complexes with an antibody against HBc. In particular the quantification of immune complexes comprising an antibody against HIRA, HIRA and HBc is preferably done by Western blot with an antibody against HBc. In particular the quantification of immune complexes comprising an antibody against HBc, HBc, and HIRA is preferably done by Western blot with an antibody against HIRA.

Antibodies which can be used in these methods according to the invention are preferably the ones used in the example (see table 3).

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

Furthermore, the indefinite article "a" or "an" does not exclude a plurality.

The invention will be further illustrated in view of the following figures and examples.

FIGURES

FIG. 1. Effect of HIRA's extinction before infection on viral parameters (cccDNA, total DNA, pgRNA and total RNAs).

(A) HepG2-NTCP cells were transfected twice within 4 days, and infected with 250 vge/cell (vge: virus genome copies or equivalents) of HBV at day 4, then harvested 2 days later. Total intracellular HBV DNA and RNA was extracted and subjected to qPCR for cccDNA, total HBV DNA, pgRNA (pregenome RNA) and total HBV RNA quantification. After normalization to housekeeping genes, results were expressed as percentage of siLUC (CTL) transfected cells. (B, C). HepG2-NTCP cells were transfected twice within 4 days, and infected with 250 vge/cell of HBV at day 4, followed by a tenofovir (Teno) treatment (100 µM) at day 3 and 5 post-infection. Cells were then harvested at day 1, 2, 3 and 7 post-infection, and viral parameters were analyzed as mentioned above.

Figure 2:
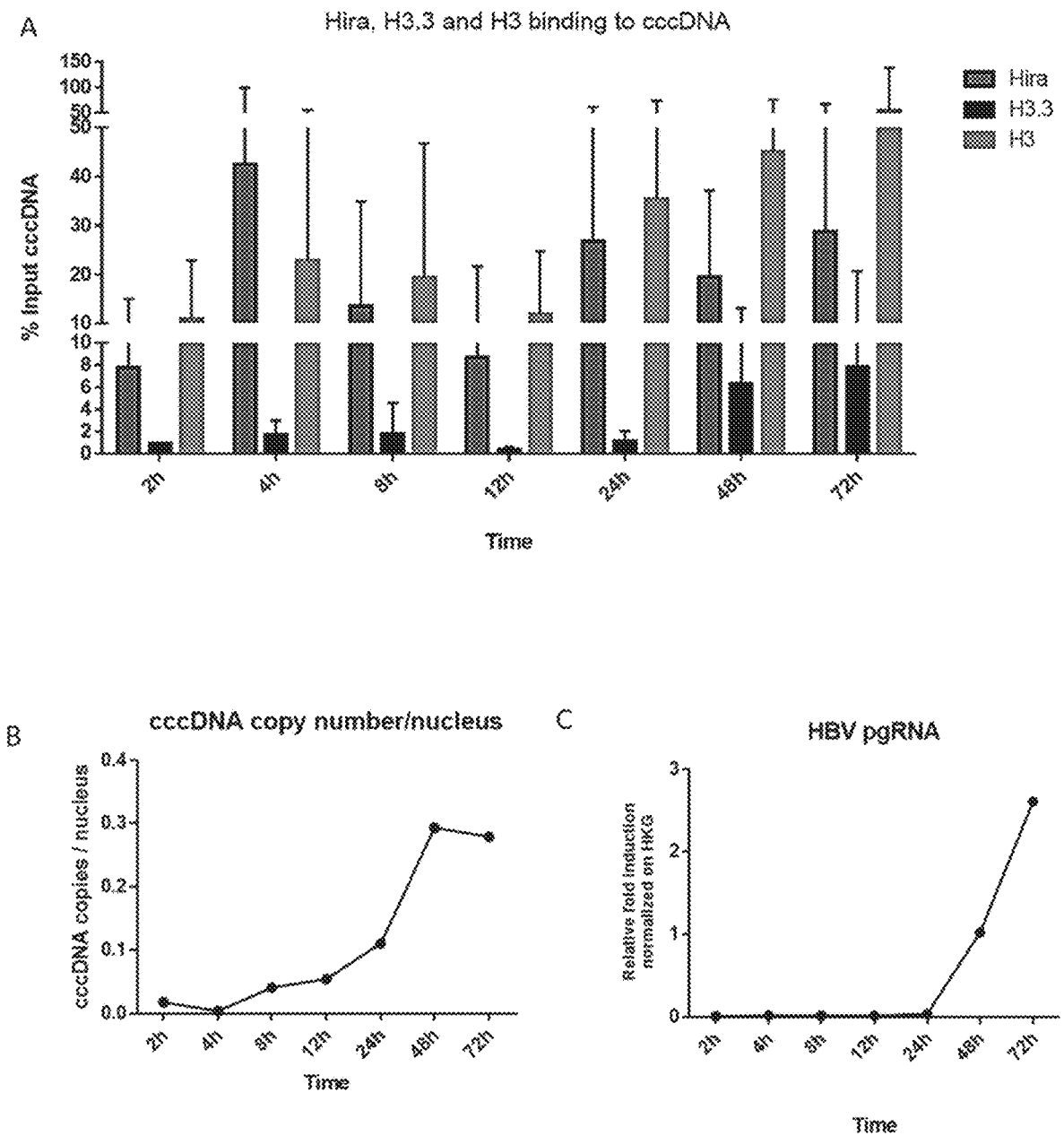
Figure 3:
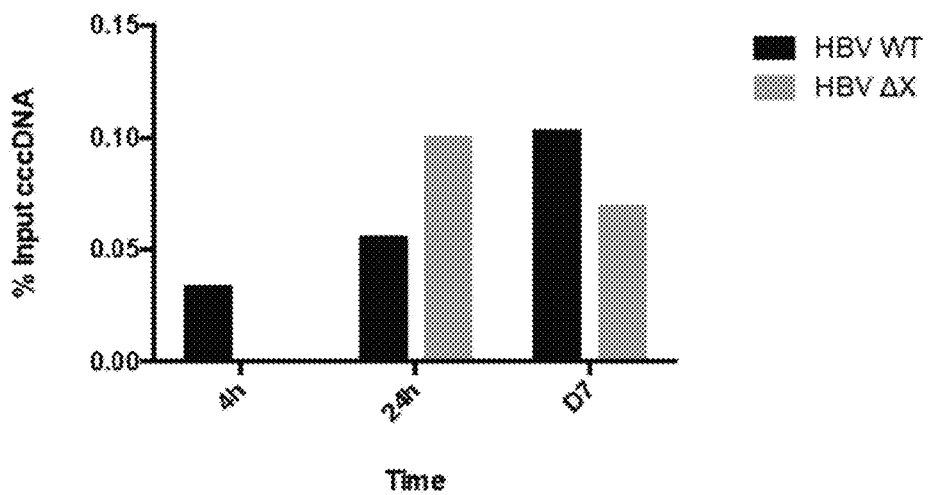
Figure 3:
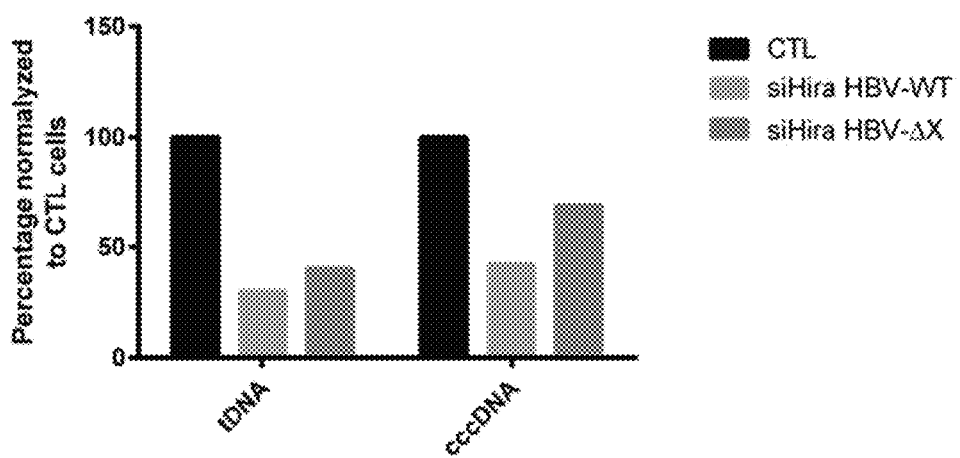

FIG. 2: Assessment of HIRA, histone H3 and variant H3.3 binding on cccDNA (A) HepG2-NTCP cells were infected with 250 vge/cell of HBV from 2 hours to 3 days. After crosslinking and nuclear extraction, ChIP experiments were performed using antibodies against HIRA, panH3 and H3.3 histone variant. On those same cells, total intracellular HBV DNA was extracted, T5 digested and analyzed by cccDNA qPCR (B). Total HBV RNA was extracted too, retrotranscribed and pgRNA appearance was analysed by qPCR (C). HKG=housekeeping gene FIG. 3: Evaluation of HBx involvement in HIRA's binding to cccDNA and in cccDNA establishment.

(A) Primary human hepatocytes were infected with 250 vge/cell of HBV wild-type (WT) or ΔHBx virus from 4 hours to 7 days. After crosslinking and nuclear extraction, ChIP experiments were performed using antibodies against HIRA. (B) PHH were transfected twice within 4 days, and infected with 250 vge/cell of HBV wild-type or ΔHBx virus at day 4, for 2 days. Total intracellular HBV DNA was extracted, followed by qPCR quantification of cccDNA and total HBV DNA (tDNA).

Figure 4:
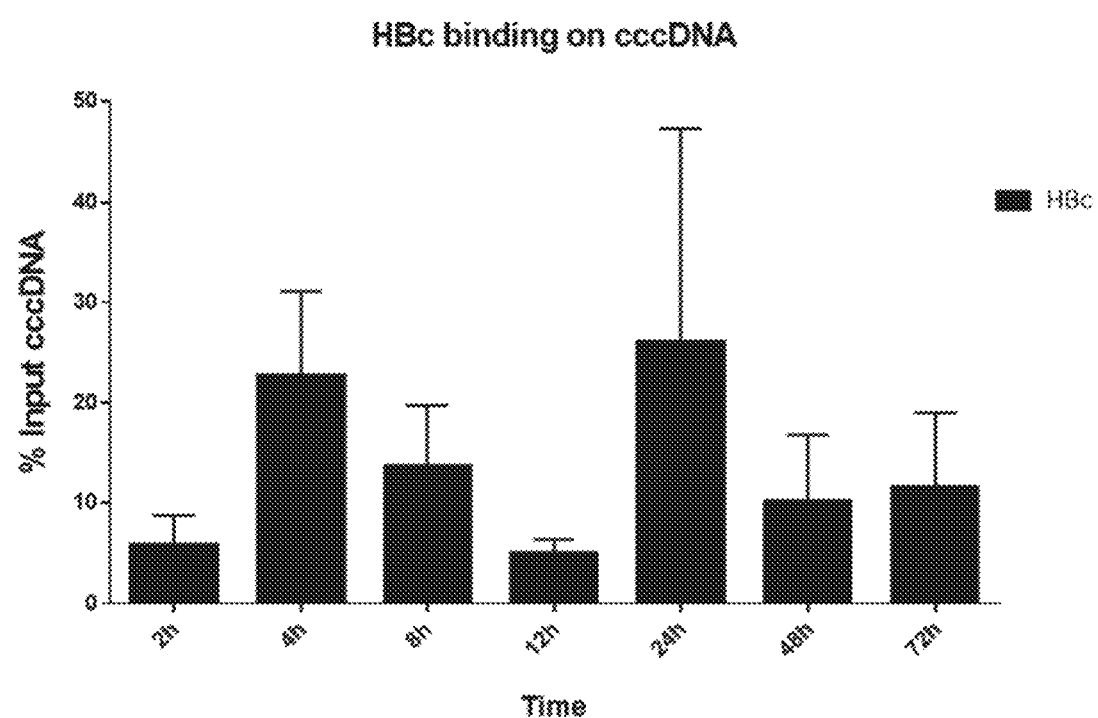

FIG. 4: Evaluation of HIRA interaction with HBV core protein.

HepG2-NTCP cells were infected with 250 vge/cell of HBV from 2 hours to 3 days. After crosslinking and nuclear extraction, ChIP experiments were performed using antibodies against HBc protein.

FIG. 5: Effect of HIRA's downregulation before infection on viral cccDNA establishment.

(A) Experimental timeline for HIRA silencing. HepG2-NTCP cells were transfected two-times with siRNA anti HIRA or a non-targeting siRNA and then inoculated for 16 h with HBV at MOI of 250 vge/cell in the presence of 4% PEG8000. Cells were harvested for analysis 2 days after infection. (B) HIRA mRNA and protein expression after siRNA transfection was determined at the moment of infection (D0 pi) and at cells harvesting (D2 pi), by real-time qPCR (left panel) and Western blot (right panel). Results of densitometric analysis is shown under the image. (C) cccDNA amount at day 2 pi (post infection) was measured by qPCR (left panel) and Southern Blotting (right panel). HIRA mRNA expression was normalized over the housekeeping gene Gusb and expressed as percentage of transfection reagent (TRA) treated cells. Actin protein served as loading control for Western Blotting analysis. cccDNA amount was expressed as percentage of transfection reagent (TRA) treated cells. In Southern Blotting, HBV and mitochondrial DNA were revealed using DIG-coupled probes (See Materials and Methods section). Mitochondrial DNA was used as internal loading control. Specificity of cccDNA band is demonstrated by linearization after digestion with EcoRI. Densitometric analysis of cccDNA band normalized over mitochondrial DNA signal is shown under the image.

Figure 6:
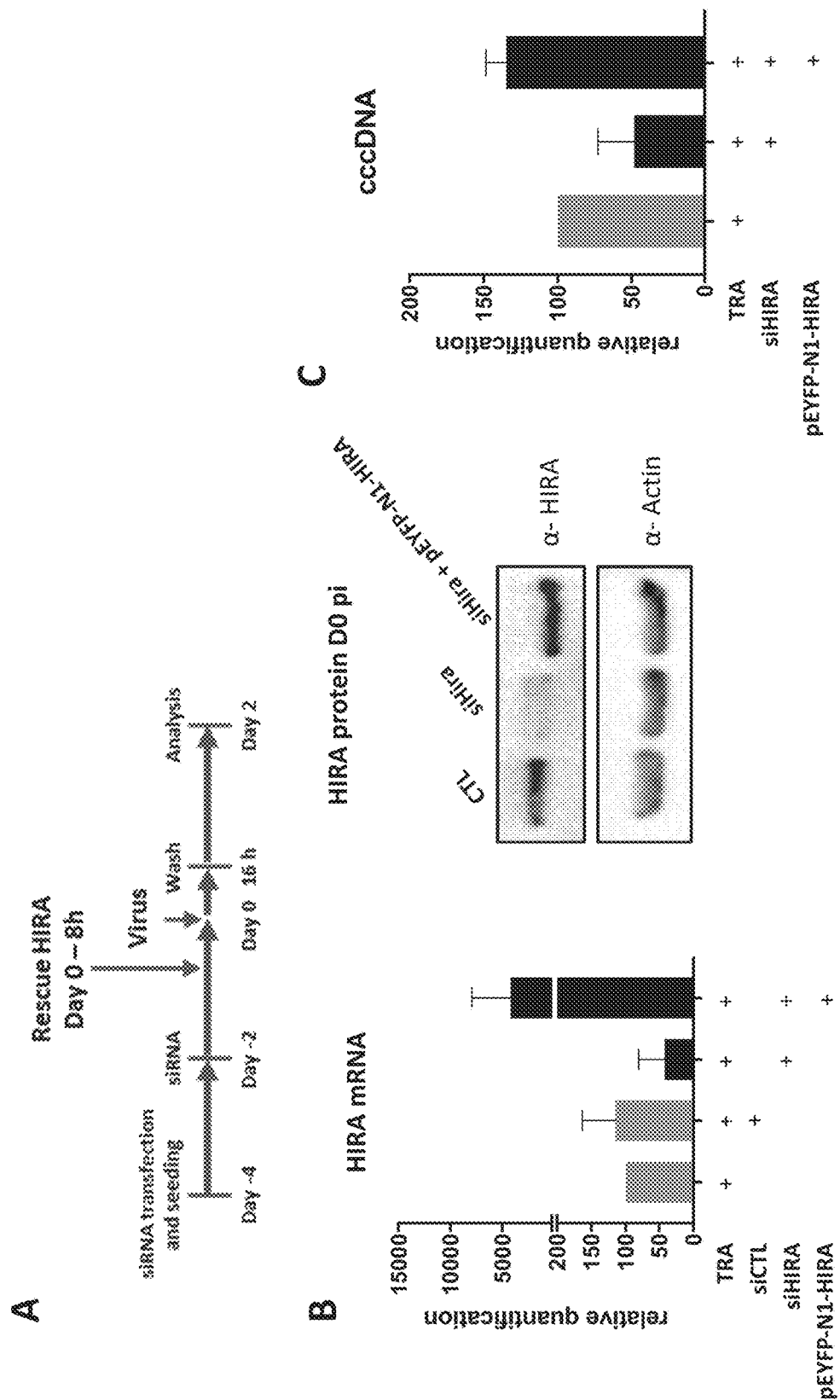

FIG. 6: HIRA Transcomplementation rescues cccDNA establishment.

(A) Experimental timeline for rescue of HIRA expression after silencing. HepG2-NTCP cells were transfected two-times with siRNA anti HIRA or a non-targeting siRNA (see Material and Methods) and then transfected with pEYFP-N1-HIRA before inoculation with HBV at MOI of 250 vge/cell in the presence of 4% PEG8000 for 16 h. The cells were harvested for analysis 2 days after infection. (B) HIRA mRNA and protein expression after siRNA transfection was determined at the moment of infection and at cells harvesting, by real-time qPCR (left panel) and Western blot (right panel). (C) cccDNA amount at day 2 pi was measured by qPCR. HIRA mRNA expression was normalized over the housekeeping gene Gusb and expressed as percentage of transfection reagent (TRA) treated cells. Actin protein served as loading control for Western Blotting analysis. cccDNA amount was expressed as percentage of transfection reagent (TRA) treated cells.

FIG. 7: Assessment of HIRA and histone variant H3.3 binding on cccDNA

HepG2-NTCP cells were infected at MOI of 250 vge/cell in the presence of 4% PEG8000 for up to 16 h and then extensively washed and cultured for the indicated time points before ChIP analysis using antibodies against HIRA (A), H3.3 (B), RNA Polymerase II (C), E2F (D), Brdu (G), and RPA70 (H). E2F ChIP was used as negative control. Immunoprecipitated cccDNA was quantified by qPCR and expressed as percentage of Input after normalization over NoAb condition. (E-F) qPCR quantification of viral cccDNA, and 3.5 Kb RNA in HepG2-NTCP-infected cells. cccDNA quantification was normalized over b-globin quantity, while relative RNA amount was calculated by normalizing over the housekeeping gene GUSB expression. Graphs represent the mean of at least three independent experiments. NoAb: no antibody; LLoD: lower limit of detection.

Figure 8:
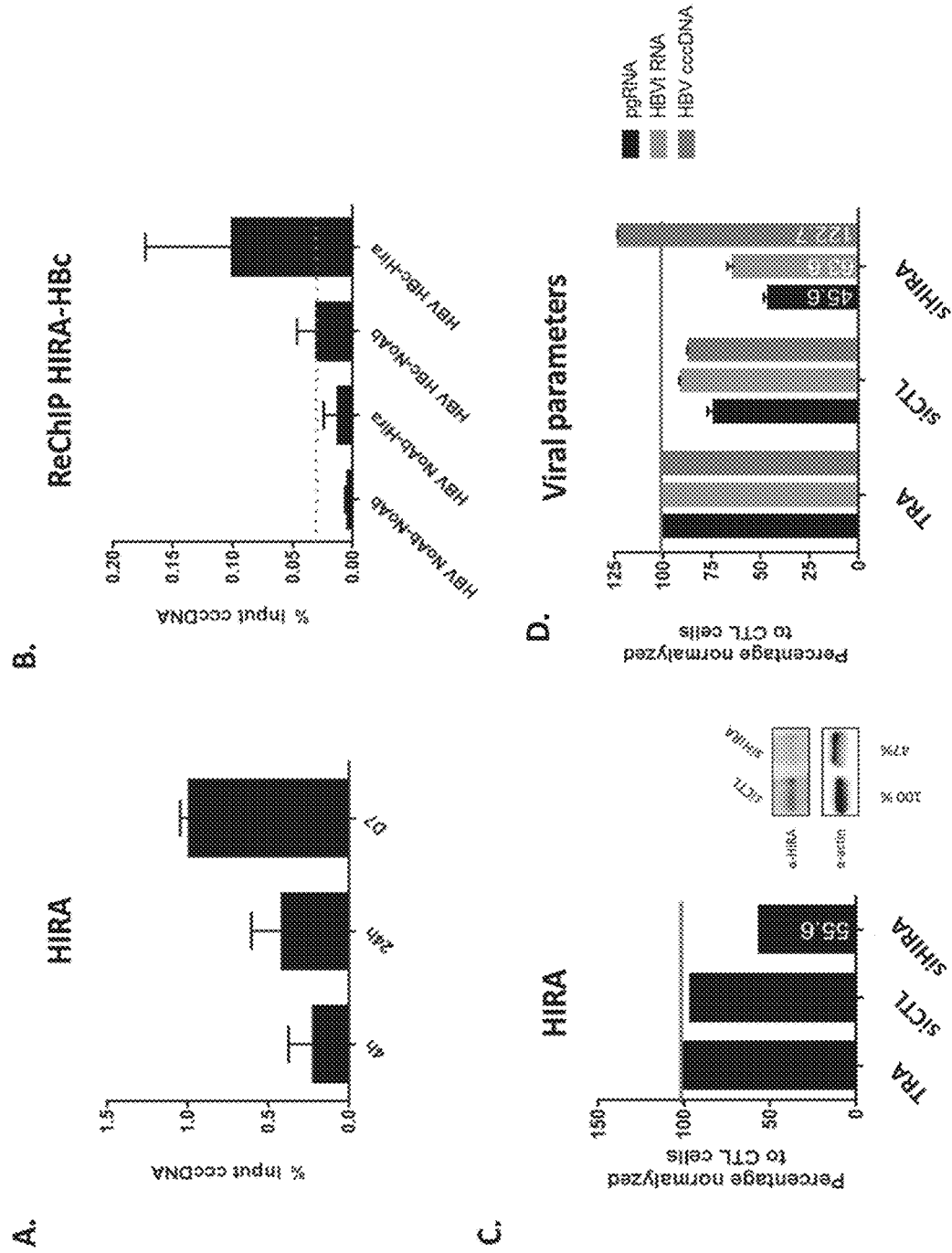

FIG. 8: Effect of HIRA's downregulation during chronic infection.

Figure 9:
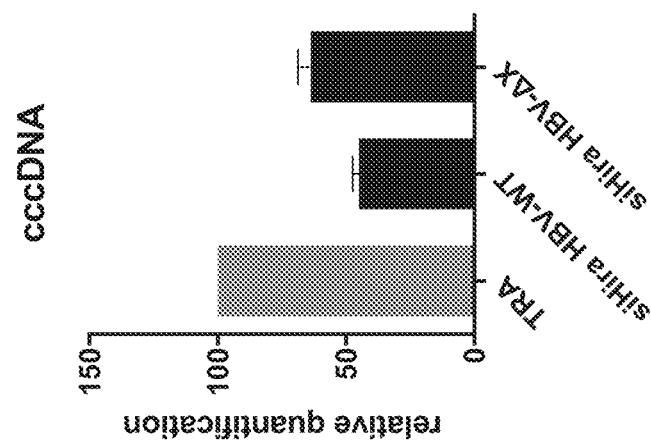
Figure 9:
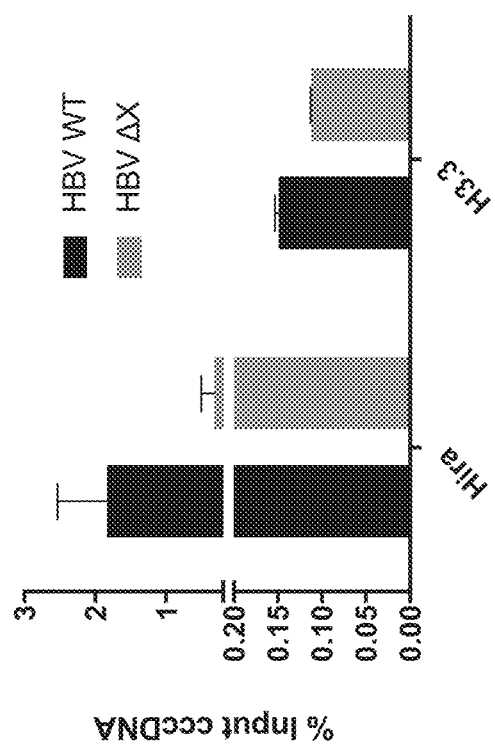

HepG2-NTCP cells were infected at MOI of 250 vge/cell in the presence of 4% PEG8000 for up to 16 h and then extensively washed and cultured for the indicated time points before ChIP analysis using antibodies against HIRA (A) or against HIRA and then against HBc (B). Immunoprecipitated cccDNA was quantified by qPCR and expressed as percentage of Input. (C-D) Silencing experiments were performed onto an established infection. HepG2-NTCP cells were infected with HBV at MOI of 250 vge/cell in the presence of 4% PEG8000. After 5 days, cells were transfected two-times with siRNA anti HIRA or a non-targeting siRNA. Cells were harvested 48 h after the second transfection (i.e. day 9 post-infection). (C) HIRA mRNA expression after siRNA transfection was determined by real-time qPCR. HIRA mRNA expression was normalized over the housekeeping gene Gusb and expressed as percentage of transfection reagent (TRA) treated cells. (D) cccDNA amount was measured by qPCR. cccDNA amount was expressed as percentage of transfection reagent (TRA) treated cells. NoAb: no antibody;

FIG. 9: Evaluation of HBx involvement in HIRA's binding to cccDNA and in cccDNA establishment.

(A) HepG2-NTCP cells were infected at MOI of 250 vge/cell in the presence of 4% PEG8000 for 4 h. The levels of HIRA and H3.3 on cccDNA were analyzed by ChIPqPCR. (B) HepG2-NTCP cells were transfected with siRNA against HIRA according to the experimental timeline shown in FIG. 6A and inoculated for 16 h with HBV at MOI of 250 vge/cell in the presence of 4% PEG8000. Cells were harvested for analysis 2 days after infection. cccDNA amount at day 2 pi was measured by qPCR and expressed as percentage of transfection reagent (TRA) treated cells.

FIG. 10: Evaluation of HIRA interaction with HBV core protein.

(A) HepG2-NTCP cells were infected at MOI of 250 vge/cell in the presence of 4% PEG8000 up to 16 h and then extensively washed and cultured for the indicated time points before ChIP analysis using an antibody against HBc. The levels of HBc on cccDNA were analyzed through the infection kinetics by ChIPqPCR. (B) The simultaneous presence of HIRA and HBc on the same cccDNA molecule was assessed by sequential ChIPqPCR 24 h after infection using an antibody against HIRA first and then an antibody anti HBc for immunoprecipitation. (C) Proximity between HBc and HIRA was assessed by proximity ligation assay (PLA) in HBV-infected HepG2-NTCP cells 24 hours post-infection. PLA signals are indicated by arrows. Uninfected HepG2-NTCP cells and infected HepG2-NTCP cells stained with only HBc or HIRA antibodies were used as negative controls (right panels). (D) Co-immunoprecipitation between and HIRA was realized in HepaRG-TR-HBc cells treated for 48 h with 10 µg/ml tetracyclin to induce HBc expression. Cell lysates were immunoprecipitated with an antibody against HBc and subjected to Western Blotting analysis with an antibody anti HBc and HIRA. Lysates from HepaRG-TR-HBc cells not treated with tetracyclin were used as negative control.

EXAMPLES

Example 1: Study of the Role of HIRA

Materials and Methods siRNA Transfection
siRNA (Individual: ON-TARGETplus HIRA siRNA; ON-TARGETplus LUC siRNA, Dharmacon) (Table 2) for HIRA and Luciferase (10 nM) were transfected in HepG2-NTCP cells and PHH before infection, using Lipofectamine RNAiMAX (ThermoFisher), following manufacturer's protocol.

TABLE 2

ON-TARGETplus siRNA sequences

| Target | Name | Sequence | SEQ ID number |
|---|---|---|---|
| ON-TARGETplus HIRA | siHIRA | GGAUAACACUGUCGUCAUC | SEQ ID NO: 1 |
| ON-TARGETplus LUC | siLUC | GAUUAUGUCCGGUUAUGUA | SEQ ID NO: 7 |

Cell Culture, HBV Infection and Analysis of Viral Parameters During Replication
HepG2-NTCP cells were seeded at 105 cells/cm$^2$ in DMEM medium supplemented with penicillin (Life Technology), streptomycin (Life Technology), sodium pyruvate (Life Technology), 5% Fetal Calf Serum (FCS; Fetalclone II™, PERBIO). The day after, medium was renewed and complemented with 2.5% DMSO (SIGMA). After 72 h, cells were infected at a multiplicity of infection of 250 in the presence of 4% PEG800 for 16 h. Cells were then extensively washed with PBS and maintained in complete DMEM medium containing 2.5% DMSO until harvesting. Intracellular accumulation of viral RNA and DNA, secretion of HBe and HBs antigens were monitored by RT-qPCR, qPCR and southern blotting, and ELISA, respectively. Briefly, HBeAg and HBsAg were quantified in culture medium by ELISA, using a chemiluminescence immunoassay kit (Autobio, China) following manufacturer's instructions. Total DNA was purified from infected cells using MasterPure™ Complete DNA Purification Kit (Epicentre). To increase the specificity of HBV cccDNA detection, 3 nuclease digestion was performed using 10 U of T5 exonuclease (Epicentre) at 37° C. for 45 minutes on 500 ng of total DNA, before selective cccDNA qPCR, based on the use of primers (and probes) spanning the nick in the HBV rcDNA and hybridizing to its "gap region"(see table 1).

Total RNA was extracted from infected cells using NucleoSpin® RNA kit (Macherey-Nagel) and retro-transcribed into cDNA using SuperScript III reverse transcriptase according to manufacturer's instructions (Invitrogen, Carlsbad, USA). Real-time PCR for total HBV DNA and cccDNA was performed using an Applied QuantStudio 7 machine and TaqMan Advanced Fast Master Mix or SYBR Green Master Mix (see examples of primers and probes, table 1).

Hirt Procedure and Southern Blot Analyses
DNA was extracted following a modified Hirt procedure (Hirt B. Selective extraction of polyoma DNA from infected mouse cell cultures. J Mol Biol. 1967). 90 µg of DNA were subjected to Southern blot analyses using a mix of DIG-labeled probes, an AP conjugated anti-DIG antibody (Roche) and CDP-Star® (Roche) according to the manufacturer's instructions.

Chromatin Immunoprecipitation (ChIP)
ChIP experiments were carried out on infected cells from 2 h to 3 days post-infection. Cells were washed in phosphate buffered saline (PBS), and incubated for 15 minutes with 1% formaldehyde at 37° C. and quenched with 0.125 M Glycine. For nuclear extracts preparation, cells were lysed in lysis buffer (PIPES 5 mM, KCl 85 mM, NP-40 0.5%, PMSF 1 mM, Protease inhibitor cocktail (PIC) 1×). After douncing (10 times) and centrifugation, nuclei were resuspended in sonication buffer (SDS 1%, EDTA 10 mM, Tris-HCl pH 8 50 mM, PMSF 1 mM, PIC 1×). After sonication, chromatin was cleaned in Ripa buffer with Protein A Sepharose, and then subjected to overnight immunoprecipitation at 4° C. using 2-5 µg of antibodies. Immune complexes were, then, incubated 2 h with protein G agarose beads at 4° C., washed, and eluted in Tris-HCl pH 8 10 mM, EDTA 5 mM, NaCl 50 mM, SDS 1%, Proteinase K 50 ug, PIC 1×. Immunoprecipitated DNA was extracted and quantified by qPCR using cccDNA specific primers (see table 1). Samples were normalized to Input DNA using the ΔCt method were ΔCt=Ct (input)−Ct (immunoprecipitation) and expressed as percentage of the Input.

Co-Immunoprecipitation
Co-immunoprecipitation experiments were carried out on HepaRG-TR-HBc cells, in which the expression of HBc protein can induced upon doxycycline treatment (10 µg/ml)). Nuclear extraction and antibody incubation was performed as for ChIP experiments (see above). Immune complexes were then incubated 2 h with protein G agarose beads at 4° C., washed, and eluted in 2×Laemmli buffer (65.8 mM Tris-HCl, pH 6.8, 2.1% SDS, 26.3% (w/v) glycerol, 0.01% bromophenol blue) to release and denature the proteins. Whole cell lysates (Input) were incubated with 6×Laemmli buffer. Proteins were separated on standard 12% gradient gels and blotted on a nitrocellulose membrane. Blots were blocked 1 hour with 5% milk in PBS and stained with primary antibody in blocking buffer overnight at 4° C. (HIRA 1:500, HBc 1:500). After primary antibody incubation, blots were washed 3× with TBS-Tween (TBST, 0.2M Tris-HCl 1.5M NaCl, 0.05 Tween 20), stained with secondary antibodies for 1 hour at room temperature and washed again 3 times with TBST. Detection occurred using Biorad Clarity Western ECL and the ChemiDoc XRS system (Biorad).

Proximity Ligation Assay

Proximity ligation assay (PLA) was performed on HepG2-NTCP infected cells according to manufacturer's instructions (DU092014 Duolink®, DUO92004 Duolink®, DUO92002 Duolink®, and DUO82040 Duolink®). Briefly, after fixation by 4% PFA 30 minutes at room temperature (RT), and quenching by 1M glycine, cells were permeabilized for 30 minutes at RT with PBS-Triton 0.3%, and then blocked 30 minutes at 37° C. with blocking buffer. Cells were incubated with the two primary antibodies overnight at 4° C. PLA probes were diluted and added to the coverslips for 1 hour at 37° C. After a 30 minutes ligation step at 37° C., the amplification was performed for 100 minutes at 37° C. Finally, coverslips were mounted onto slips with Mounting Medium with DAPI.

Antibodies

ChIP and Co-immunoprecipitation experiments were performed using the following antibodies:

TABLE 3

Antibodies used for PLA, co-immunoprecipitation (co-IP), ChIP and western blotting experiments (WB)

| Target | Company | Dilution |
| --- | --- | --- |
| HBc for PLA, co-IP and ChIP | Invitrogen SC2362651 | 4 µg |
| HBc for WB | Dako B0586 | 1:500 |
| HIRA for PLA, ChIP and WB | Abcam Ab20655 | 2.5 µg |
| panH3 for ChIP | Diagenode C15200011 | 2.5 µg |
| H3.3 for ChIP | Abcam Ab62642 | 5 µg |

Results

The inventors investigated the effect of HIRA downregulation on HBV cccDNA establishment and replication by siRNA mediated knockdown (siHIRA). The efficiency of HIRA knockdown was determined by quantification of HIRA mRNA levels after transfection, using a Luciferase siRNA (CTL) as a control. Transfection of siHIRA reduced by nearly 70% endogenous level of HIRA mRNA from 24 h to 96 h post-transfection, and remained at nearly 50% of extinction at day 2 post-infection (FIG. 1A) while Luciferase siRNA had no effect on HIRA mRNA levels.

qPCR analysis showed that knockdown of HIRA expression resulted in the reduction of 50% of cccDNA levels, accompanied by a decrease of intracellular total HBV DNA, total HBV RNAs and pregenomic (pg)RNA, in particular (FIG. 1A). Southern Blotting analysis confirmed the reduction in cccDNA, especially at day 3 post-infection. On the contrary, rcDNA levels remained stable, ruling out a defect in viral entry and suggesting a possible either incomplete or delayed rcDNA to cccDNA transition. The use of Tenofovir (Teno), a nucleoside analogue blocking pgRNA to rcDNA conversion, allowed us to inhibit the recycling of nucleocapsids from the cytoplasm. In this condition, cccDNA amounts remained downregulated also at day 7 post infection, when HIRA mRNA went back to basal levels (FIG. 1B), while, in untreated cells, cccDNA levels went back to basal levels (FIG. 1C). These results suggest that HIRA extinction leads not to a delayed, but to a blockade of cccDNA formation that needs nucleocapsids recycling to be overcome.

Chromatin Immunoprecipitation analysis showed that HIRA was bound to cccDNA already at 2 hours post-infection (FIG. 2A). This binding was persistent until 3 days post-infection. The recruitment of HIRA was concomitant with the deposition of histone variant H3.3. Indeed, the presence of H3.3 on cccDNA was observable after 2 hours post-infection, stable until 24 hours, and increased after 48 hours of infection.

Concerning total histone H3, component of stable nucleosomes, it showed an early recruitment between 2 h and 8 h post-infection and, then, a second wave of binding, slower and more progressive, beginning from 12 h and still increasing at 72 h post-infection. The increase in H3.3 and total H3 binding to cccDNA after 48 h of infection correlated with the beginning of cccDNA transcriptional activity, as indicated by pgRNA kinetic of appearance by qPCR (FIG. 2B, C).

To investigate a possible involvement of the viral protein HBx in HIRA-mediated cccDNA establishment, the inventors took advantage of a ΔHBx virus strain. Chromatin Immunoprecipitation analysis showed that HIRA binding to cccDNA was not affected by the absence of HBx protein (FIG. 3A). Similarly, siRNA mediated knockdown of HIRA in absence of X protein expression resulted in a similar reduction of cccDNA levels and total intracellular HBV DNA compared to WT virus (FIG. 3B).

By ChIP experiments, the inventors were able to demonstrate that HBc binds to cccDNA as early as after 2 hours of infection (FIG. 4), correlating with the recruitment of HIRA on the HBV minichromosome (FIG. 2A). The inventors decided, then, to investigate a possible interaction between the two proteins. Firstly, by co-immunoprecipitation, the inventors showed that HIRA was able to interact with HBc in an HepaRG cell line expressing HBc in an inducible manner. Secondly, performing Proximity Ligation Assay (PLA) in HBV infected hepatocytes, the inventors showed an interaction between HBc and HIRA as soon as 24 h post-infection.

Altogether, the inventors' results suggest that chromatinization of incoming viral DNA is a very early event, requiring the histone chaperone HIRA, thus suggesting that the inhibition of HIRA interaction with cccDNA could represent a new therapeutic target to be investigated. While HBx is not required for this process, HBc could play a major role, thus opening a new perspective for the investigation of a specific role for HBc in recruiting HIRA to the cccDNA.

Example 2: Complement Study of the Role of HIRA

Materials & Methods

Production of Wild-Type and Mutated HBV Viral Inoculum

HBV inoculum was prepared from filtered HepAD38 cells (Ladner et al., 1997) or K6 (HBx negative virus; Lucifora et al., JHep 2011) supernatants by polyethyleneglycol-MW-8000 (PEG8000, SIGMA) precipitation (8% final). Viral stock with a titer reaching at least $1\times10^{10}$ vge/mL was tested endotoxin free and used for infection.

Cell Culture and HBV Infection

HepG2-NTCP cells were seeded at $10^5$ cells/cm$^2$ in DMEM medium supplemented with penicillin (Life Technology), streptomycin (Life Technology), sodium pyruvate (Life Technology), 5% Fetal Calf Serum (FCS; Fetalclone II™, PERBIO). The day after, medium was renewed and complemented with 2.5% DMSO (SIGMA). After 72 h, cells were infected at a multiplicity of infection of 250 in the presence of 4% PEG800 for up to 16 h and then extensively washed and cultured for the indicated time points in complete DMEM medium containing 2.5% DMSO until harvesting. Intracellular accumulation of viral RNA and DNA were monitored by RT-qPCR, qPCR and Southern Blotting. For de novo DNA synthesis analysis, cells were treated with 20 µM BrdU (Sigma) 24 h hours before infection and during viral inoculation.

Analysis of Viral Parameters During Replication and qPCR

Total DNA was purified from infected cells using MasterPure™ Complete DNA Purification Kit (Epicentre). Total HBV DNA was quantified using TaqMan® Gene Expression assay ID: Pa03453406_s1. To increase the specificity of HBV cccDNA detection, qPCR was preceded by a nuclease digestion using 10 U of T5 exonuclease (Epicentre) for 500 ng of total DNA. Selective cccDNA qPCR was performed using primers and probes spanning the "gap region" in the HBV rcDNA (see Table 4). Serial dilutions of an HBV monomer plasmid (pHBV-EcoRI) were used as standard for quantification. For normalization, the number of human hepatocytes was estimated by measuring human b-globin (TaqMan® assay ID Hs00758889_s1) while human genomic DNA (Roche Applied Science, Mannheim, Germany) was used as a standard curve for quantification. Total RNA was extracted from infected cells using NucleoSpin® RNA kit (Macherey-Nagel) and retro-transcribed using SuperScript III reverse transcriptase according to manufacturer's instructions (Invitrogen, Carlsbad, USA). 3.5 Kb viral RNA (comprising pgRNA and pre-core RNA) and total HBV RNA were amplified using previously described primers and probes (Table 4). Primers for HIRA mRNA expression are listed in Table 4. The expression of the human housekeeping gene GUSb (TaqMan® assay ID Hs00939627_m1) was used for normalization. Real-time PCRs were performed using an Applied QuantStudio 7 machine and TaqMan Advanced Fast Master Mix or SYBR Green Master Mix (ThermoFischer).

Table 4

Primers and probes sequences used for Taqman and SYBRgreen qPCR.

| Target | Name | Sequence |
|---|---|---|
| cccDNA | cccDNA Taqman | CCGTGTGCACTTCGCTTCA (SEQ ID NO: 4) |
| cccDNA | cccDNA Taqman | GCACAGCTTGGAGGCTTGA (SEQ ID NO: 5) |
| cccDNA | cccDNA Taqman Probe | [6FAM]CATGGAGACCACCGTGAACGCCC[BBQ] (SEQ ID NO: 6) |
| pgRNA | pgRNA Taqman | GGAGTGTGGATTCGCACTCCT (SEQ ID NO: 8) |
| pgRNA | pgRNA Taqman | AGATTGAGATCTTCTGCGAC (SEQ ID NO: 9) |
| pgRNA | pgRNA Taqman Probe | [6FAM]AGGCAGGT0000TAGAAGAAGAACTCC[BBQ] (SEQ ID NO: 10) |
| GUSb | FW_gusb | CGTGGTTGGAGAGCTCATTTGGAA (SEQ ID NO: 11) |
| GUSb | RV_gusb | ATTCCCCAGCACTCTCGTCGGT (SEQ ID NO: 12) |
| Hira | Hira Forward | GGCCTCGGAAGGACTCTC (SEQ ID NO: 2) |
| Hira | Hira Reverse | AGACAGACACATGGCCTCCT (SEQ ID NO: 3) |

Plasmid and siRNA Cell Transfection pEYFP-N1-HIRA construct was transfected in HepG2-NTCP cells and PHH using TransIT-2020 (Mirus Bio LLC) following manufacturer's protocol. siRNA targeting HIRA (ON-TARGETplus HIRA siRNA GGAUAACACUGUCGUCAUC, SEQ ID NO: 1) and the corresponding siRNA mutated in position 9-11 (siRNA CTL: GGAUAACAGACUCGUCAUC, SEQ ID NO: 13) to serve as negative control were transfected at 10 nM concentration in HepG2-NTCP cells and PHH using Lipofectamine RNAiMAX reagent (ThermoFisher), following manufacturer's instructions.

Hirt Extraction and Southern Blot Analysis

DNA was extracted following a modified Hirt procedure. 90 µg of DNA were subjected to Southern blot analyses using a mix of DIG-labeled probes (synthesized using primers listed below and the "PCR DIG probe synthesis kit" (Roche)), an AP conjugated anti-DIG antibody (Roche) and CDP-Star® (Roche) according to the manufacturer's instructions. Mitochondrial DNA served as internal loading control.

TABLE 5

DIG-labeled HBV DNA probes sequences

| Target | Name | Sequence |
|---|---|---|
| HBV | HBV-F1 | TAGCGCCTCATTTTGTGGGT (SEQ ID NO: 14) |
|  | HBV-R1 | CTTCCTGTCTGGCGATTGGT (SEQ ID NO: 15) |
|  | HBV-F2 | TAGGACCCCTTCTCGTGTTA (SEQ ID NO: 16) |
|  | HBV-R2 | CCGTCCGAAGGTTTGGTACA (SEQ ID NO: 17) |
|  | HBV-F3 | ATGTGGTATTGGGGGCCAAG (SEQ ID NO: 18) |
|  | HBV-R3 | GGTTGCGTCAGCAAACACTT (SEQ ID NO: 19) |
|  | HBV-F4 | TGGACCTTTTCGGCTCCTC (SEQ ID NO: 20) |
|  | HBV-R4 | GGGAGTCCGCGTAAAGAGAG (SEQ ID NO: 21) |
|  | HBV-F5 | GTCTGTGCCTTCTCATCTG (SEQ ID NO: 22) |
|  | HBV-R5 | AGGAGACTCTAAGGCTTCC (SEQ ID NO: 23) |
|  | HBV-F6 | TACTGCACTCAGGCAAGCAA (SEQ ID NO: 24) |
|  | HBV-R6 | TGCGAATCCACACTCCGAAA (SEQ ID NO: 25) |

TABLE 5-continued

DIG-labeled HBV DNA probes sequences

| Target | Name | Sequence |
|---|---|---|
| | HBV-F8 | AGACGAAGGTCTCAATCGCC (SEQ ID NO: 26) |
| | HBV-R8 | ACCCACAAAATGAGGCGCTA (SEQ ID NO: 27) |

TABLE 6

DIG-labeled mitochondrial DNA probes sequences

| Target | Name | Sequence |
|---|---|---|
| Mitochondrial DNA | Fw-huND1 | CCCTACTTCTAACCTCCCTGTTCTTAT (SEQ ID NO: 28) |
| | Rw-huND1 | CATAGGAGGTGTATGAGTTGGTCGTA (SEQ ID NO: 29) |
| | Fw-huND5 | ATTTTATTTCTCCAACATACTCGGATT (SEQ ID NO: 30) |
| | Rw-huND5 | GGGCAGGTTTTGGCTCGTA (SEQ ID NO: 31) |
| | Fw-huATP6 | CATTTACACCAACCACCCAACTATC (SEQ ID NO: 32) |
| | Rw-huATP6 | CGAAAGCCTATAATCACTGTGCC (SEQ ID NO: 33) |

Chromatin Immunoprecipitation (ChIP)

ChIP experiments were carried out at the indicated time points (from 30 minutes to 72 hours) post-infection. Briefly, cells were washed in phosphate buffered saline (PBS), and incubated for 15 minutes with 1% formaldehyde at 37° C. and quenched with 0.125 M Glycine. For nuclear extracts preparation, cells were lysed in lysis buffer (PIPES 5 mM, KCl 85 mM, NP-40 0.5%, PMSF 1 mM, Protease inhibitor cocktail (PIC) 1×). After douncing (10 times) and centrifugation, nuclei were resuspended in sonication buffer (SDS 1%, EDTA 10 mM, Tris-HCl pH 8 50 mM, PMSF 1 mM, PIC 1×). After sonication, chromatin was cleaned in Ripa buffer with Protein A Sepharose, and then subjected to overnight immunoprecipitation at 4° C. using 2-5 µg of antibodies indicated in Table 4 or No Antibody. Immune complexes were, then, incubated for 2 h with protein G agarose beads at 4° C., washed, and eluted in Tris-HCl pH 8 10 mM, EDTA 5 mM, NaCl 50 mM, SDS 1%, Proteinase K 50 µg, PIC 1×. Immunoprecipitated DNA was extracted and quantified by qPCR using cccDNA specific primers (see table 4). Samples were normalized to input DNA using the ΔCt method were ΔCt=Ct (input)−Ct (immunoprecipitation) and expressed as percentage of the input after normalization over No Antibody signal.

Sequential Chromatin Immunoprecipitation

Cells were processed as for ChIP experiment until the overnight immunoprecipitation. Immune complexes were, then, incubated 2 h with protein G agarose beads at 4° C., washed and eluted in 10 mM DTT. Eluted samples were then re-exposed to overnight immunoprecipitation at 4° C. using 2-5 µg of antibodies in Re-ChIP buffer (1% Triton X-100; 2 mM EDTA; 150 mM NaCl; 20 mM Tris-HCl pH 8). Immune complexes were, then, processed as for a classic chromatin immunoprecipitation described above.

Western Blotting

Cells were lysed in RIPA buffer supplemented with PIC 1× and PMSF 1×. Proteins were migrated in 4-20% mini-PROTEAN@ TGX stain-Free™ Precast Gel (Bio-Rab Laboratories) and transferred onto a nitrocellulose membrane (Bio-Rab Laboratories). Blots were blocked 1 hour with 5% milk in TBS (1×Tris Buffered Saline (Sigma)) and stained with primary antibody in blocking buffer overnight at 4° C. After primary antibody incubation, blots were washed 3× with TBST (1×TBS with 0.1% Tween 20), stained with HRP-conjugated secondary antibodies for 1 hour at room temperature and washed again 3 times with TBST. Detection occurred using Biorad Clarity Western ECL and the Chemi-Doc XRS system (Biorad). Antibodies are listed in Table 7.

Protein Co-Immunoprecipitation (Co-IP)

Protein co-immunoprecipitation experiments were carried out on HepaRG-TR-HBc cell lines. HBc expression was induced by doxycycline treatment (10 µg/ml) for 48 h. Nuclear extraction and antibody incubation was performed as for ChIP experiments. Immune complexes were then incubated 2 h with protein G agarose beads at 4° C., washed, and eluted in 2×laemmli buffer (65.8 mM Tris-HCl, pH 6.8, 2.1% SDS, 26.3% (w/v) glycerol, 0.01% bromophenol blue) to release and denature the proteins. $^{1}/_{10}$ of cell lysate, serving as input condition, was incubated with 6×laemmli buffer and subjected to western blotting analysis together with immunoprecipitated samples, as previously detailed. Antibodies used are listed in Table 7.

Proximity Ligation Assay

Proximity ligation assay (PLA) was performed on infected HepG2-NTCP cells according to manufacturer's instructions (DUO92014 Duolink®, DUO92004 Duolink®, DUO92002 Duolink®, and DUO82040 Duolink®). Briefly, after fixation by 4% PFA 30 minutes at RT, and quenching by 1M glycine, cells were permeabilized for 30 minutes at RT with PBS-Triton 0.3%, and then blocked 30 minutes at 37° C. with blocking buffer. Cells were incubated with the two primary antibodies overnight at 4° C. (see Table 7). PLA probes were diluted and added to the coverslips for 1 hour at 37° C. After a ligation step of 30 minutes at 37° C., the amplification was performed during 100 minutes at 37° C. Finally, coverslips were mounted onto slips with Mounting Medium with DAPI. Images were acquired with the confocal microscope zeiss LSM 780 NLO.

TABLE 7

Antibodies used for co-immunoprecipitation, ChIP and western blotting experiments

| Target | Company | Dilution |
|---|---|---|
| HBc for PLA, co-IP and ChIP | Invitrogen | 4 µg |
| Hira for PLA, ChIP and WB | Abeam Ab20655 | 2.5 µg/1:500 |
| H3.3 for ChIP | Abeam Ab62642 | 5 µg |
| RNA Polymerase II for ChIP | Diagenode | 1 µg |
| RPA 70 for ChIP | Abeam Ab79398 | 5 µg |
| BrdU for ChIP | BD Pharmingen | 5 µg |
| E2F for ChIP | Santa Cruz | 5 µg |
| beta-actin for WB | Abcam Ab6276 | 1:10000 |
| HBc for WB | Dako B0586 | 1:500 |

Results

Figure 5A:
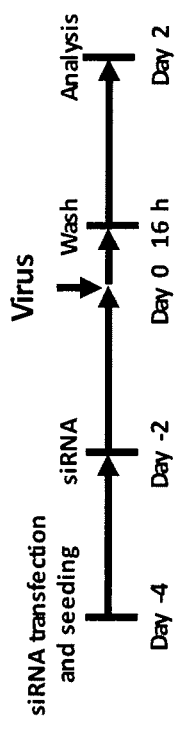
Figure 5B:
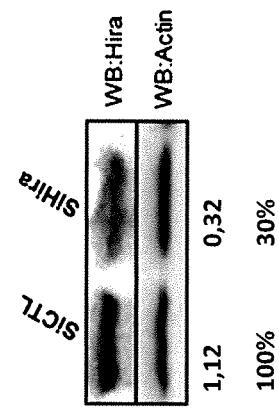
Figure 5B:
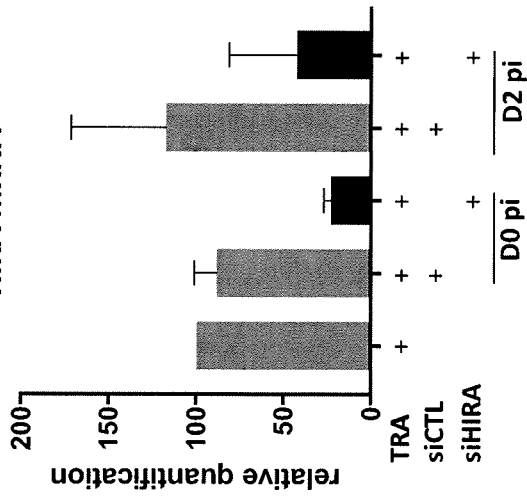
Figure 5C:
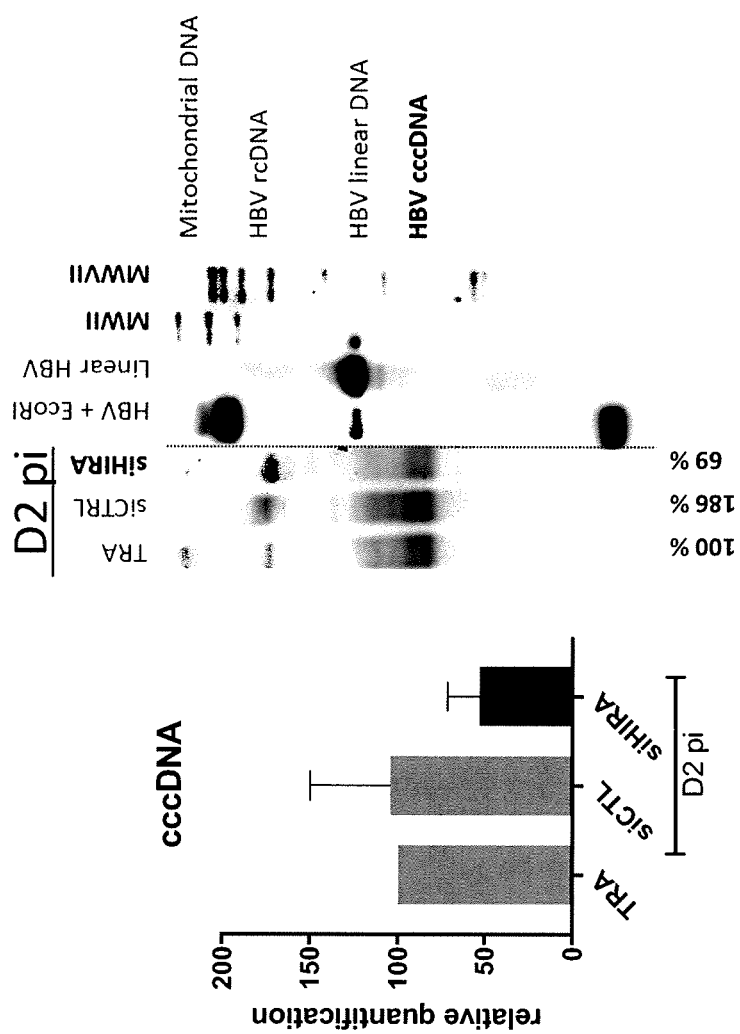

The inventors investigated the effect of HIRA downregulation on HBV cccDNA establishment and replication by siRNA mediated knockdown (siHIRA). The efficiency of HIRA knockdown was determined by quantification of HIRA mRNA levels after transfection, using an anti-HIRA siRNA mutated in position 9 and 11 (CTL) as a control. Transfection of siHIRA reduced by nearly 70% endogenous level of HIRA mRNA and protein levels while Luciferase siRNA had no effect on HIRA mRNA or protein expression (FIG. 5B).

qPCR analysis showed that knockdown of HIRA expression resulted in the reduction of 50% of cccDNA levels measured by qPCR and Southern Blotting (FIG. 1C). On the contrary, rcDNA levels remained stable, ruling out a defect in viral entry and suggesting a possible either incomplete or delayed rcDNA to cccDNA transition.

To further confirm the involvement of HIRA in HBV cccDNA establishment, the HIRA expression was rescued after silencing in HepG2-NTCP cells by transfecting the pEYFP-N1-HIRA construct 8 h before HBV infection (FIG. 6A). Analysis of HIRA expression by both qRT-PCR and Western Blotting, confirmed the restoration of its levels both at the mRNA and protein level (FIG. 6B). In parallel, cccDNA amount were evaluated by qPCR and went back to the level of non-silenced controls (TRA) (FIG. 6C).

Figure 7D:
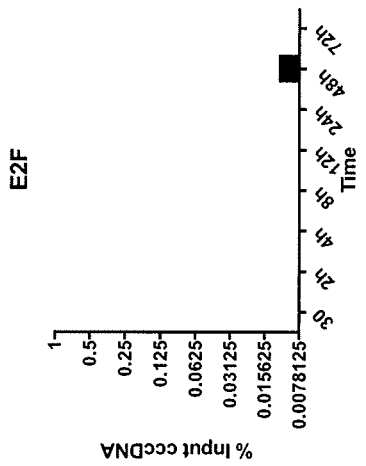

Chromatin Immunoprecipitation analysis showed that HIRA was bound to cccDNA already at 30 minutes post-infection (FIG. 7A). This binding was persistent until 3 days post-infection. The recruitment of HIRA was concomitant with the deposition of histone variant H3.3 (FIG. 7B). Indeed, the presence of H3.3 on cccDNA was observable after 30 minutes post-infection, stable until 24 hours, and increased after 48 hours of infection.

Figure 7H:
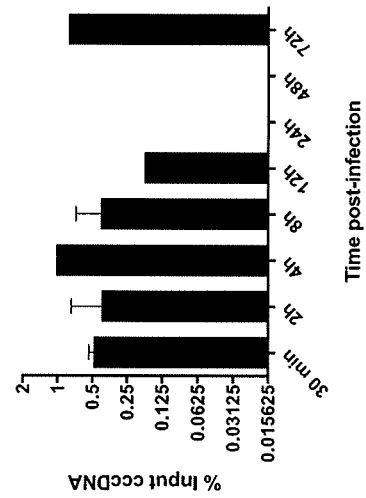
Figure 7C:
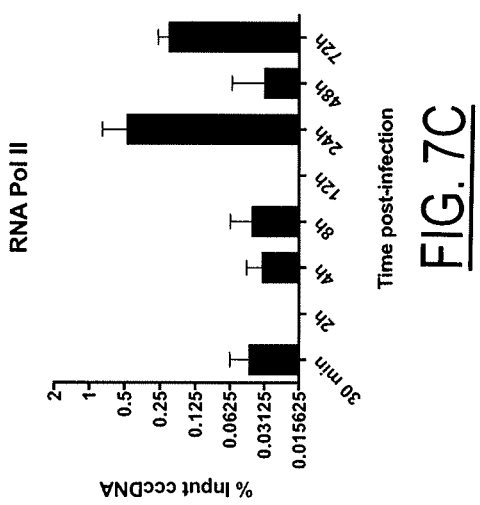

The increase in H3.3 binding to cccDNA after 48 h of infection correlated with the amplification of cccDNA pool (FIG. 7E) and the beginning of cccDNA transcriptional activity, as indicated by pgRNA kinetic of appearance by qPCR (FIG. 7F) and RNA Pol II recruitment to cccDNA (FIG. 7C).

Figure 7G:
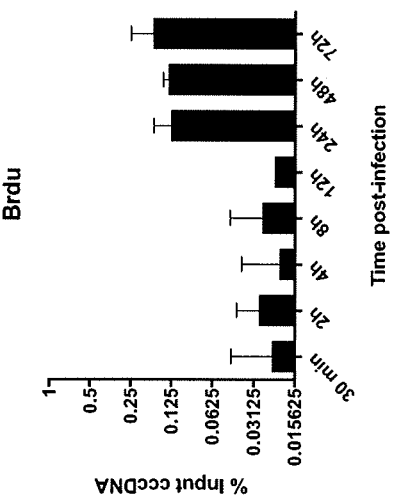

In an attempt to define the kinetics of H3.3 incorporation by HIRA during the rcDNA to cccDNA conversion, the kinetic of incorporation of BRdU and the recruitment of RPA70 to cccDNA was investigated (FIG. 7G-H). Since rcDNA to cccDNA conversion is thought to involve host cell DNA repair pathways and the activity of POLK for the completion of plus-strand and ligation of both strands HepG2-NTCP cells were treated with BrdU before and during virus inoculation and then ChIP analysis was performed using a BrdU-specific antibody to detect new nucleotides incorporation into cccDNA. As shown in FIG. 7G, no significant BrdU incorporation is found between 30 minutes and 12 h, corresponding to the initial phase of cccDNA formation from incoming HBV genome. On the contrary, BrdU incorporation increases concomitantly to the beginning of transcription and synthesis of new rcDNA. Interestingly, the inventors found that RPA70, was recruited to cccDNA only from 30 minutes to 12 h to come back again at 72 h, when newly synthesized rcDNA could be recycled to the nucleus to be converted into cccDNA (FIG. 7H). Altogether, these ChIP data suggest that histone deposition occurs on a cccDNA precursor which has both DNA strands completed but at least one of them not ligated, which corresponds to the main PF-rcDNA species found in the nucleus of infected cells. To further confirm this hypothesis, immunoprecipitated DNA in FIG. 7 was also amplified with primers located in a HBV double stranded region common to PF-rcDNA and cccDNA. The analysis showed no differences in the percentage of immunoprecipitated HBV DNA with respect to cccDNA, thus confirming that the immunoprecipitated material is mostly constituted by HBV DNA with complete strands (data not shown).

By ChIP experiment, (FIG. 8A), going from 4 hours, to 7 days post-infection, the inventors could show that HIRA was found bound to cccDNA even when infection is considered chronic. Furthermore, sequential ChIP showed that HBc was found bound onto the same cccDNA molecule as HIRA, as compared to negative controls (No antibody-No antibody, No antibody-HIRA, HBc-No antibody, FIG. 8B). Finally, to investigate the functional presence of HIRA onto cccDNA at that time of infection, silencing experiments were performed onto an established infection. Indeed, after 5 days of infection, cells were transfected with siHIRA (a first time at day 5, a second time at day 7, to obtain a better knock-down). At day 9 post-infection, proteins, RNA and DNA were harvested. RNA and protein expression analysis showed a strong effect of HIRA knock-down (FIG. 8C). 3.5 Kb RNA and total HBV RNA levels appeared impaired by HIRA knock-down (FIG. 8D). These preliminary results are suggesting an additional role for HIRA concerning cccDNA biology, where HIRA could be involved in the maintenance of cccDNA transcriptional activity.

To investigate a possible involvement of the viral protein HBx in HIRA-mediated cccDNA establishment, the inventors took advantage of a ΔHBx virus strain. Chromatin Immunoprecipitation analysis showed that HIRA binding to cccDNA was not affected by the absence of HBx protein (FIGS. 3A and 9A). Similarly, siRNA mediated knockdown of HIRA in absence of X protein expression resulted in a similar reduction of cccDNA levels and total intracellular HBV DNA compared to WT virus (FIGS. 3B and 9B).

Figure 10D:
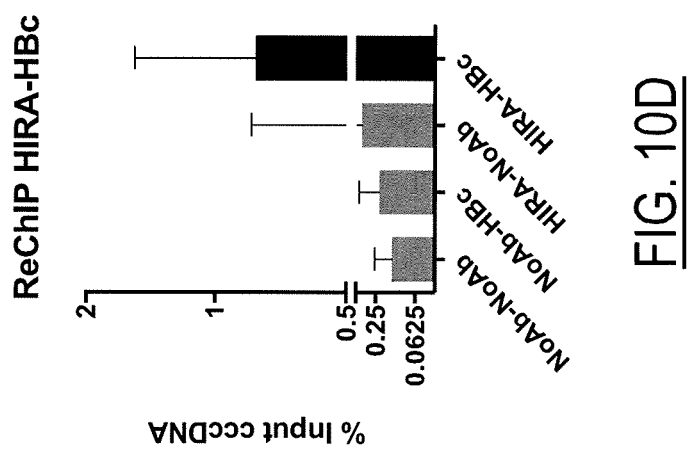

By ChIP experiments, the inventors were able to demonstrate that HBc binds to cccDNA as early as after 30 minutes of infection (FIG. 10A), correlating with the recruitment of HIRA on the HBV minichromosome (FIG. 7A). The inventors decided, then, to investigate a possible interaction between the two proteins. Firstly, by co-immunoprecipitation, the inventors showed that HIRA was able to interact with HBc in an HepaRG cell line expressing HBc in an inducible manner, suggesting that the two proteins are able to associate also in the absence of viral genome (FIG. 10B). Secondly, performing Proximity Ligation Assay (PLA) in HBV infected hepatocytes, the inventors showed an interaction between HBc and HIRA as soon as 24 h post-infection (FIG. 10C). Moreover, sequential ChIP experiments indicated that HBc and HIRA could bind to the same cccDNA molecule 24 h post-infection (FIG. 10D).

Example 3: In Silico Study of HBc Interaction with HIRA

The Protein Data Bank (PDB) is a universal protein database that contains crystal structures and information about the structure and functions of proteins. This information was used to retrieve the crystal structures of HBc dimer (accession number: 1GQT) and a portion of HIRA protein (accession number: 2i32, as available on Jul. 26, 2018).

PRISM server (PRotein Interactions by Structural Matching) is a resource portal for the bioinformatics which offers computational methods and approaches for large scale structural modelling of protein-protein interactions. PRISM server was used to perform prediction of protein-protein interaction and allowed to uncover 4 different predictive models of HBc/HIRA interaction. The server includes the tools for predicting interacting structure, interface, and amino acids possible interactions between the two proteins, as listed in Table 8. For example, in the selected model 1, Isoleucine 466 of HIRA (as represented in sequence SEQ ID NO: 34) could be interacting with Cystein 136 of HBc protein (as represented in sequence SEQ ID NO: 35).

This in silico experiment shows a predicted interaction of HBc and HIRA through 4 different possible interfaces, requiring from −5.73 to −1.05 kJ/mol energy to interact. The more negative the energy required is, the more efficient the protein-protein interaction will potentially be.

TABLE 8

Table of predictive interface residues contact between HIRA and HBc.

| HIRA (UniProtKB P54198) | Possible interaction with | HBc (UniProtKB Q89714) |
|---|---|---|
| ILE 466 | | CYS 136 |
| ILE 466 | | LEU 137 |

TABLE 8-continued

Table of predictive interface residues contact between HIRA and HBc.

| HIRA (UniProtKB P54198) | Possible interaction with | HBc (UniProtKB Q89714) |
|---|---|---|
| CYS 465 | | CYS 136 |
| ILE 466 | | HIS 80 |
| LEU 464 | | THR 138 |
| LEU 464 | | LEU 137 |
| LEU 464 | | THR 171 |
| ILE 466 | | GLY 140 |
| ILE 466 | | ARG 141 |
| CYS 465 | | GLY 140 |
| CYS 465 | | PHE 139 |
| ILE 466 | | SER 78 |

The invention claimed is:

1. A method for preventing the onset of infection with hepatitis B virus (HBV) or treating an infection with hepatitis B virus (HBV) comprising administering a therapeutically effective amount of an histone chaperone HIRA inhibitor to a subject in need thereof,
   wherein said inhibitor is selected from the group consisting of
     an inhibitor of HIRA expression chosen from siRNA and antisense oligonucleotides; and
     an inhibitor of HIRA interaction with cccDNA and/or an inhibitor of HIRA interaction with HBV capsid protein (HBc) chosen from aptamers, antibodies and antibody fragments.

2. The method according to claim 1, wherein said HBV virus is an HBV of any genotype.

3. The method according to claim 1, wherein said inhibitor is an inhibitor of HIRA expression, or an inhibitor of HIRA interaction with HBV covalently-closed-circular (ccc) DNA and/or HBV capsid protein (HBc).

4. The method according to claim 1, wherein said inhibitor is an inhibitor of HIRA expression chosen from siRNA and antisense oligonucleotides.

5. The method according to claim 1, wherein said inhibitor is an inhibitor of HIRA interaction with cccDNA and/or an inhibitor of HIRA interaction with HBV capsid protein (HBc) chosen from aptamers, antibodies and antibody fragments.

6. The method according to claim 1, wherein the histone chaperone HIRA inhibitor is formulated in a pharmaceutical composition.

7. The method according to claim 1, wherein said inhibitor reduces cccDNA amount in the nucleus of hepatocytes infected with HBV.

8. The method according to claim 1, wherein said HIRA inhibitor is administered by topical route, oral route, intranasal route, intraocular route, parenteral route, or by intramuscular, subcutaneous, intravenous, intraperitoneal or local injections.

9. The method according to claim 1, wherein said inhibitor is:
   a siRNA with a nucleotide sequence which is at least 85% identical to the sequence GGAUAACACUGUCGUCAUC (SEQ ID NO: 1).

10. The method according to claim 1, wherein said inhibitor is an antibody targeting HBV capsid protein.

11. The method according to claim 1, wherein said inhibitor is an antibody, an antibody fragment or an aptamer binding to:
- amino acids 464-466 of HIRA, or
- amino acids 78-80 of the HBV capsid protein, or
- amino acids 136-141 (SEQ ID NO: 36) of the HBV capsid protein, or
- amino acid 171 of the HBV capsid protein.

12. An in vitro screening method for the identification of a candidate compound suitable for preventing the onset of infection with hepatitis B virus (HBV) or treating an infection with hepatitis B virus comprising:
  a) infecting hepatocytes with HBV, in the presence and in the absence of a candidate compound;
  b) measuring the binding of HIRA to cccDNA or HBc in hepatocytes infected with HBV, in the presence and in the absence of the candidate compound;
  c) comparing the level of binding of HIRA to cccDNA or HBc in hepatocytes infected with HBV in the presence the candidate compound, with the level of binding of HIRA to cccDNA or HBc in hepatocytes infected with HBV in the absence of the candidate compound; and
  d) identifying the candidate compound as suitable for preventing and/or treating an infection with hepatitis B virus if the level of binding of HIRA to cccDNA or HBc in hepatocytes infected with HBV in the presence the candidate compound is decreased compared with the level of binding of HIRA to cccDNA or HBc in hepatocytes infected with HBV in the absence of the candidate.

13. The in vitro screening method according to claim 12, wherein the measure of the binding of HIRA to cccDNA or HBc comprises:
  a) nuclear extraction of hepatocytes;
  b) sonication of obtained nuclei;
  c) immunoprecipitation with an antibody against HIRA or with an antibody against HBc;
  d) purification of obtained immune complexes; and
  e) quantification of immune complexes comprising HIRA and cccDNA or HIRA and HBc.

14. The in vitro screening method according to claim 13, wherein the quantification of immune complexes for measuring the binding of HIRA to cccDNA is done by quantitative PCR using cccDNA specific primers.

15. The in vitro screening method according to claim 13, wherein the quantification of immune complexes for measuring the binding of HIRA to HBc is done by Western blot of immune complexes with an antibody against HIRA and/or by Western blot of immune complexes with an antibody against HBc.

* * * * *